(12) United States Patent
Perez Saez et al.

(10) Patent No.: US 12,365,715 B2
(45) Date of Patent: Jul. 22, 2025

(54) RECOMBINANT CHORIONIC GONADOTROPIN, PROCEDURE FOR PREPARATION, PHARMACEUTICAL COMPOSITIONS AND USES OF THE SAME

(71) Applicants: Syntex S.A., Ciudad Autonoma de Buenos Aires (AR); Alejandro Dario Abentin, Luis Guillon-Buenos Aires (AR)

(72) Inventors: Juan Manuel Perez Saez, Ciudad Autonoma de Buenos Aires (AR); Leonardo Edmundo Bussmann, Florida (AR)

(73) Assignees: Syntex S.A., Buenos Aires (AR); Alejandro Dario Abentin, Buenos Aires (AR)

( * ) Notice: Subject to any disclaimer, the term of this patent is extended or adjusted under 35 U.S.C. 154(b) by 591 days.

(21) Appl. No.: 17/638,118

(22) PCT Filed: Aug. 30, 2019

(86) PCT No.: PCT/EP2019/073277
§ 371 (c)(1),
(2) Date: Feb. 24, 2022

(87) PCT Pub. No.: WO2021/037384
PCT Pub. Date: Mar. 4, 2021

(65) Prior Publication Data
US 2022/0289810 A1    Sep. 15, 2022

(51) Int. Cl.
*C07K 14/59* (2006.01)
*A61K 38/00* (2006.01)

(52) U.S. Cl.
CPC .............. *C07K 14/59* (2013.01); *A61K 38/00* (2013.01)

(58) Field of Classification Search
CPC .................................. C07K 14/59; A61K 38/00
See application file for complete search history.

(56) References Cited

U.S. PATENT DOCUMENTS

2022/0267401 A1*  8/2022  Baruffi ................. C07K 14/575

FOREIGN PATENT DOCUMENTS

| WO | WO 98/21238 A1 | 5/1998 |
| WO | WO 2009/073474 A2 | 6/2009 |

(Continued)

OTHER PUBLICATIONS

Christakos et al., "Pregnant Mare Serum Gonadotropin: Purification and Physicochemical, Biological, and Immunological Characterization", The Journal of Biological Chemistry, 1979, pp. 4253-4261, vol. 254, No. 10, (nine (9) pages).

(Continued)

*Primary Examiner* — Louise W Humphrey
*Assistant Examiner* — Rachel Emily Martin
(74) *Attorney, Agent, or Firm* — Crowell & Moring LLP

(57) ABSTRACT

This invention relates to a recombinant single chain chorionic gonadotropin polypeptide, having an amino acid sequence encoding the beta chain and the alpha chain of the equine chorionic gonadotropin linked to one or more sequences that include glycosylation sites, which results in excellent in vitro and in vivo activity. The DNA molecules that encode the recombinant polypeptide are also taught, an expression vector comprising these DNA molecules, compositions comprising the recombinant protein and methods for preparing them are also disclosed.

10 Claims, 12 Drawing Sheets

Specification includes a Sequence Listing.

Expression vectors encoding Beta/Alpha fusion protein variants with different linkers

(56) References Cited

FOREIGN PATENT DOCUMENTS

| WO | WO 2009/073574 A1 | 6/2009 |
|---|---|---|
| WO | WO 2017/112987 A1 | 7/2017 |

OTHER PUBLICATIONS

Bousfield et al., "Identification of Twelve O-Glycosylation Sites in Equine Chorionic Gonadotropin β and Equine Luteinizing Hormone β by Solid-Phase Edman Degradation", Biology of Reproduction, 2001, pp. 136-147, vol. 64, (12 pages).
Galet et al., "The Postendocytotic Trafficking of the Human Lutropin Receptor is Mediated by a Transferable Motif Consisting of the C-Terminal Cysteine and an Upstream Leucine", Molecular Endocrinology, Feb. 2004, pp. 434-446, vol. 18, No. 2, (13 pages).
Allen et al., "The Origin of the Equine Endometrial Cups: I. Production of PMSG by Fetal Trophoblast Cells", J. Reprod. Fert., 1972, pp. 313-316, vol. 29, (five (5) pages).
Combarnous et al., "Equine Follicle-Stimulating Hormone: Purification, Acid Dissociation, and Binding to Equine Testicular Tissue", The Journal of Biological Chemistry, Sep. 25, 1981, pp. 9567-9572, vol. 256, No. 18, (six (6) pages).
Galet et al., "Expression of a Single βα Chain Protein of Equine LH/CG in Milk of Transgenic Rabbits and its Biological Activity", Molecular and Cellular Endocrinology, 2000, pp. 31-40, vol. 174, (10 pages).
Jablonka-Shariff et al., "Expression and Bioactivity of a Single Chain Recombinant Equine Luteinizing Hormone (reLH)", Theriogenology, 2007, pp. 311-320, vol. 67, (10 pages).
Bo et al., "Superovulatory Response to a Single Subcutaneous Injection of Folltronpin-V in Beef Cattle", Theriogenology, 1994, pp. 42, vol. 963-975, (13 pages).
Adams et al., "Association Between Surges of Follicle-Stimulating Hormone and the Emergence of Follicular Waves in Heifers", Journals of Reproduction & Fertility Ltd, 1992, pp. 177-188, vol. 94, (12 pages).
Alfuraiji et al., "Superovulation in Cattle Using PMSG Followed by PMSG-Monoclonal Antibodies", Animal Reproduction Science, 1993, pp. 99-109, vol. 33, (11 pages).
Goulding et al., "Factors Affecting Superovulation in Heifers Treated with PMSG", Theriogenology, 1996, pp. 765-773, vol. 45, (nine (9) pages).
Ben-Menahem et al., "Single Chain Variants of the Glycoprotein Hormones and Their Receptors as Tools to Study Receptor Activation and for Analogue Design", Journal of Neuroendocrinology, 2004, pp. 171-177, vol. 16, (seven (7) pages).
Bo et al., "Identification of the Transcriptionally Active Genes of the Chorionic Gonadotropin β Gene Cluster in Vivo", The Journal of Biological Chemistry, Feb. 15, 1992, pp. 3179-3184, vol. 267, No. 5, (six (6) pages).
Sherman et al., "A Single Gene Encodes the β-Subunits of Equine Luteinizing Hormone and Chorionic Gonadotropin", Molecular Endocrinology, 1992, pp. 951-959, vol. 6, No. 6, (nine (9) pages).
Smith et al., "Equine Lutropin and Chorionic Gonadotropin Bear Oligosaccharides Terminating with $SO_4$-4-GalNAc and Siaα2,3Gal, Respectively", The Journal of Biological Chemistry, 1993, pp. 795-802, vol. 268, No. 2, (eight (8) pages).
Matsui et al., "Structural Analysis of N-Linked Oligosaccharides of Equine Chorionic Gonadotropin and Lutropin β-Subunits", Biochemistry, 1994, pp. 14039-14048, vol. 33, No. 47, (10 pages).
Klett et al., "Fast Renal Trapping of Porcine Luteinizing Hormone (pLH) Shown by $^{123}$I-scintigraphic Imaging in Rats Explains its Short Circulatory Half-Life", Reproductive Biology and Endocrinology, 2003, pp. 1-8, vol. 1, (eight (8) pages).
Stewart et al., "Pregnant Mare Serum Gonadotrophin: Ratio of Follicle-Stimulating Hormone and Luteinizing Hormone Activities Measured by Radioreceptor Assay", J. Endocr., 1976, pp. 371-382, vol. 71, (12 pages).
Min et al., "Biological Activities of Tethered Equine Chorionic Gonadotropin (eCG) and its Deglycosylated Mutants", Journal of Reproduction and Development, 2004, pp. 297-304, vol. 50, No. 3, (eight (8) pages).
Knopf et al., "Ovarian Follicular Dynamics in Heifers: Test of Two-Wave Hypothesis by Ultrasonically Monitoring Individual Follicles", Domestic Animal Endocrinology, 1989, pp. 111-119, vol. 6, No. 2, (nine (9) pages).
Nakav et al., "Homologous and Heterologous Carboxyl Terminal Peptide (CTP) Linker Sequences Enhance the Secretion of Bioactive Single-Chain Bovine LH Analogs", Exp Clin Endocrinol Diabetes, 2006, pp. 95-104, vol. 114, (10 pages).
Shiota et al., "Equine Chorionic Gonadotropin Alpha and Beta Chain Fusion Protein", Journal, Sep. 28, 1998, pp. 26, XP-002795224, (one (1) page).
Min et al., "Site-Directed Mutagenesis of Recombinant Equine Chorionic Gonadotropin/Luteinizing Hormone: Differential Role of Oligosaccharides in Luteinizing Hormone- and Follicle-Stimulating Hormone-Like Actives", Endocrine Journal, 1996, pp. 585-593, vol. 43, No. 5, (nine (9) pages).
Di Rienzo et al., "Instruction manual for a statistics software", Software estadistico Infostat, 2008, pp. 1-333, (333 pages).
International Search Report (PCT/ISA/210) issued in PCT Application No. PCT/EP2019/073277 dated Nov. 25, 2019 (four (4) pages).
Written Opinion (PCT/ISA/237) issued in PCT Application No. PCT/EP2019/073277 dated Nov. 25, 2019 (six (6) pages).
Lemke et al., "Single-Chain Human Gonadotropin Analogs Induce Follicle Development in Sheep", Journal of Endocrinology, 2008, pp. 593-600, vol. 196, XP055409301, (eight (8) pages).
Bouloux et al., "First Human Exposure to FSH-CTP in Hypogonadotrophic Hypogondal Males", Human Reproduction, 2001, pp. 1592-1597, vol. 16, No. 8, XP001080293, (six (6) pages).
Sugahara et al., "Biosynthesis of a Biologically Active Single Peptide Chain Containing the Human Common Alpha and Chorionic Gonadotropin Beta Subunits in Tandem", Proc. Natl. Acad. Sci. USA, Mar. 1995, pp. 2041-2045, vol. 92, No. 6, XP002057264, (five (5) pages).
Legardinier et al., "Biological Activities of Recombinant Equine Luteinizing Hormone/Chorionic Gonadotropin (eLH/CG) Expressed in Sf9 and Mimic Insect Cell Lines", Journal of Molecular Endocrinology, 2005, pp. 47-60, vol. 34, No. 1, XP055292939, (14 pages).

\* cited by examiner in vitro FSH Biological activity for different constructs expressed in HEK293T or CHOK1 cells

Analysis of the supernatants of the expression products in HEK293T or CHOK1 cells

Coomasie — Western Blot

10% native acrylamide gel is shown. Each lane was seeded with 17 ug of total protein. The H series are those synthesized by HEK and C cells in CHO K1. BSA 5 ug and PMSG 0.25 IU. The units corresponding to the 17 ug of mass were: 2H (pCG 2) 4 IU; 5H (pCG 5) 7.2 IU; 8H (pCG.8) 4.5 IU; 10H (pCG 10) 1.4 IU; 5C (pCG5) 0.55 IU; 8C (pCG 8) 0.22 IU.

AFSH biological activity in vitro of stably protein-producing clones.

Figure 7

Analysis of purified reCG proteins by immunoaffinity.

The eCG pattern seeded was 10 and 1 ug for staining with Coomasie and Western, constructs # 5 and # 8 were loaded with 3.5 and 0.5 ug for the same conditions.

Number of follicles (mean) according to the follicle size and the day of treatment in cows treated with eCG (Native; n = 13) or reCG (n = 14) during the period prior to removing the device with P4 (P > 0.1).

Number of follicles after removing the progesterone containing device

Number of follicles (mean) according to the follicle size and the day of treatment in cows treated with eCG (Native; n = 13) or reCG (n = 14) after removing the device with P4 (P > 0.1).

P4 levels in both treatment groups.

SEQUENCE LISTING

<160> NUMBER OF SEQ ID NOS: 12

<210> SEQ ID NO 1
<211> LENGTH: 1063
<212> TYPE: DNA
<213> ORGANISM: Artificial Sequence
<220> FEATURE:
<223> OTHER INFORMATION: Nucleotide sequence encoding NTP-BetaCTP-NTP-Alpha

<400> SEQUENCE: 1

```
atggagaccc tgcagggcct gctgctgtgg atgctgctga gcgtgggagg cgtgtgggct      60
ggcgatatcg gcctgaacat caccggcagc ggcctgaata tcacaggctc tggcctgaac     120
attaccggct ctggcctgaa tatcaccggc cctggctcta cagatatcag cagaggacca     180
ctgaggcctc tgtgccggcc tatcaacgcc accctggctg ctgagaagga ggcttgccca     240
atctgtatca cattcaccac aagcatctgc gccggctact gtccatccat ggtgcgcgtg     300
atgccagccg ctctgccagc tatccctcag ccagtgtgca cctatcggga gctgaggttc     360
gcttccatca ggctgccagg atgtccacct ggagtggacc ctatggtgtc ctttccagtg     420
gctctgtctt gccactgtgg ccctgccag atcaagacca cagactgtgg cgtgtttagg      480
gatcagccac tggcttgtgc tcctcaggct agctcctcta gcaaggatcc accctcccag     540
cccctgacca gcacatccac ccccacacct ggcgcttctc ggaggtcctc tcacccactg     600
cccatcaaga cctctggcag cggcctgaac atcacaggtt ctggcctgaa tattactggc     660
tctggcctga acatcaccgg ttccggcctg aatattaccg gcccaggctc cacatctttc     720
cccgacggcg agtttaccac acaggattgc cccgagtgta agctgaggga gaacaagtac     780
ttctttaagc tgggcgtgcc tatctatcag tgcaagggct gctgtttcag ccgggcctac     840
cctaccccag ctagaagccg caagacaatg ctggtgccta agaatatcac cagcgagtcc     900
acatgctgcg tggccaaggc tttttatccgg gtgaccgtga tgggcaacat caagctggag     960
aatcacaccc agtgctactg ttctacatgt tatcaccaca agatctgatt tcctgatgga    1020
gagtttacaa cgcaggattg cccagaaccc ccatcccaac ctc                      1063
```

<210> SEQ ID NO 2
<211> LENGTH: 335
<212> TYPE: PRT
<213> ORGANISM: Artificial Sequence
<220> FEATURE:
<223> OTHER INFORMATION: Recombinant protein NTP-BetaCTP-NTP-Alpha

<400> SEQUENCE: 2

```
Met Glu Thr Leu Gln Gly Leu Leu Leu Trp Met Leu Leu Ser Val Gly
1               5                   10                  15

Gly Val Trp Ala Gly Asp Ile Gly Leu Asn Ile Thr Gly Ser Gly Leu
            20                  25                  30

Asn Ile Thr Gly Ser Gly Leu Asn Ile Thr Gly Ser Gly Leu Asn Ile
        35                  40                  45

Thr Gly Pro Gly Ser Thr Asp Ile Ser Arg Gly Pro Leu Arg Pro Leu
    50                  55                  60

Cys Arg Pro Ile Asn Ala Thr Leu Ala Ala Glu Lys Glu Ala Cys Pro
65                  70                  75                  80

Ile Cys Ile Thr Phe Thr Thr Ser Ile Cys Ala Gly Tyr Cys Pro Ser
                85                  90                  95

Met Val Arg Val Met Pro Ala Ala Leu Pro Ala Ile Pro Gln Pro Val
            100                 105                 110

Cys Thr Tyr Arg Glu Leu Arg Phe Ala Ser Ile Arg Leu Pro Gly Cys
        115                 120                 125

Pro Pro Gly Val Asp Pro Met Val Ser Phe Pro Val Ala Leu Ser Cys
    130                 135                 140

His Cys Gly Pro Cys Gln Ile Lys Thr Thr Asp Cys Gly Val Phe Arg
145                 150                 155                 160

Asp Gln Pro Leu Ala Cys Ala Pro Gln Ala Ser Ser Ser Lys Asp
                165                 170                 175

Pro Pro Ser Gln Pro Leu Thr Ser Thr Ser Thr Pro Thr Pro Gly Ala
            180                 185                 190

Ser Arg Arg Ser Ser His Pro Leu Pro Ile Lys Thr Ser Gly Ser Gly
        195                 200                 205

Leu Asn Ile Thr Gly Ser Gly Leu Asn Ile Thr Gly Ser Gly Leu Asn
    210                 215                 220

Ile Thr Gly Ser Gly Leu Asn Ile Thr Gly Pro Gly Ser Thr Ser Phe
225                 230                 235                 240

Pro Asp Gly Glu Phe Thr Thr Gln Asp Cys Pro Glu Cys Lys Leu Arg
                245                 250                 255

Glu Asn Lys Tyr Phe Phe Lys Leu Gly Val Pro Ile Tyr Gln Cys Lys
            260                 265                 270

Gly Cys Cys Phe Ser Arg Ala Tyr Pro Thr Pro Ala Arg Ser Arg Lys
        275                 280                 285

Thr Met Leu Val Pro Lys Asn Ile Thr Ser Glu Ser Thr Cys Cys Val
    290                 295                 300

Ala Lys Ala Phe Ile Arg Val Thr Val Met Gly Asn Ile Lys Leu Glu
305                 310                 315                 320

Asn His Thr Gln Cys Tyr Cys Ser Thr Cys Tyr His His Lys Ile
                325                 330                 335
```

<210> SEQ ID NO 3
<211> LENGTH: 1023
<212> TYPE: DNA
<213> ORGANISM: Artificial Sequence
<220> FEATURE:
<223> OTHER INFORMATION: Nucleotide sequence encoding NTP-BetaCTP-CTP-Alpha

<400> SEQUENCE: 3

```
atggagaccc tgcagggcct gctgctgtgg atgctgctgt ctgtgggagg cgtgtgggct    60
ggcgatatcg gcctgaacat caccggctcc ggcctgaata tcacaggctc tggcctgaac   120
atcaccggaa gcggcctgaa tatcaccgga ccaggcagca cagatatctc ccggggacca   180
ctgaggcctc tgtgcagacc tatcaacgcc acactggccg ctgagaagga ggcttgccca   240
atctgtatca ccttcaccac atccatctgc gccggctact gtccttctat ggtgagagtg   300
atgccagccg ctctgccagc tatcccacag cccgtgtgca cctatagaga gctgcgcttc   360
gctagcatca gactgccagg atgtccacct ggagtggacc ctatggtgtc ttttccagtg   420
gctctgagct gccactgtgg ccctgccag atcaagacca cagactgtgg cgtgtttcgc   480
gatcagccac tggcttgtgc tcctcaggct agctcctcta gcaaggaccc accaagccag   540
ccactgacca gcacatccac cccaacaccc ggcgcttctc ggaggtcctc tcaccctctg   600
ccaatcaaga caagcgcccc ccaggcctct tcctctagca aggatcctcc atcccagcct   660
ctgacctcta caagcacccc aacacctgga gcttccagac gctcctctca cccactgccc   720
atcaagacct ctttcccaga cggcgagttt accacacagg attgccccga gtgtaagctg   780
cgcgagaaca agtacttctt taagctgggc gtgcctatct atcagtgcaa gggctgctgt   840
ttcagccggg cctaccctac accagctcgg tccaggaaga ccatgctggt gccaaagaat   900
atcacctccg agtctacatg ctgcgtggcc aaggctttta tccgggtgac cgtgatgggc   960
aacatcaagc tggagaatca cacccagtgc tactgttcca catgttatca ccacaagatc  1020
tga                                                                1023
```

<210> SEQ ID NO 4
<211> LENGTH: 340
<212> TYPE: PRT
<213> ORGANISM: Artificial Sequence
<220> FEATURE:
<223> OTHER INFORMATION: Recombinant protein NTP-BetaCTP-CTP-Alpha

<400> SEQUENCE: 4

Met Glu Thr Leu Gln Gly Leu Leu Leu Trp Met Leu Leu Ser Val Gly
1               5                   10                  15

Gly Val Trp Ala Gly Asp Ile Gly Leu Asn Ile Thr Gly Ser Gly Leu
                20                  25                  30

Asn Ile Thr Gly Ser Gly Leu Asn Ile Thr Gly Ser Gly Leu Asn Ile
            35                  40                  45

Thr Gly Pro Gly Ser Thr Asp Ile Ser Arg Gly Pro Leu Arg Pro Leu
        50                  55                  60

Cys Arg Pro Ile Asn Ala Thr Leu Ala Ala Glu Lys Glu Ala Cys Pro
65                  70                  75                  80

Ile Cys Ile Thr Phe Thr Thr Ser Ile Cys Ala Gly Tyr Cys Pro Ser
                85                  90                  95

Met Val Arg Val Met Pro Ala Ala Leu Pro Ala Ile Pro Gln Pro Val
                100                 105                 110

Cys Thr Tyr Arg Glu Leu Arg Phe Ala Ser Ile Arg Leu Pro Gly Cys
            115                 120                 125

Pro Pro Gly Val Asp Pro Met Val Ser Phe Pro Val Ala Leu Ser Cys
        130                 135                 140

His Cys Gly Pro Cys Gln Ile Lys Thr Thr Asp Cys Gly Val Phe Arg
145                 150                 155                 160

Asp Gln Pro Leu Ala Cys Ala Pro Gln Ala Ser Ser Ser Ser Lys Asp
                165                 170                 175

```
Pro Pro Ser Gln Pro Leu Thr Ser Thr Ser Thr Pro Gly Ala
            180                 185                 190

Ser Arg Arg Ser Ser His Pro Leu Pro Ile Lys Thr Ser Ala Pro Gln
        195                 200                 205

Ala Ser Ser Ser Lys Asp Pro Pro Ser Gln Pro Leu Thr Ser Thr
    210                 215                 220

Ser Thr Pro Thr Pro Gly Ala Ser Arg Arg Ser Ser His Pro Leu Pro
225                 230                 235                 240

Ile Lys Thr Ser Phe Pro Asp Gly Glu Phe Thr Thr Gln Asp Cys Pro
                245                 250                 255

Glu Cys Lys Leu Arg Glu Asn Lys Tyr Phe Phe Lys Leu Gly Val Pro
            260                 265                 270

Ile Tyr Gln Cys Lys Gly Cys Cys Phe Ser Arg Ala Tyr Pro Thr Pro
        275                 280                 285

Ala Arg Ser Arg Lys Thr Met Leu Val Pro Lys Asn Ile Thr Ser Glu
    290                 295                 300

Ser Thr Cys Cys Val Ala Lys Ala Phe Ile Arg Val Thr Val Met Gly
305                 310                 315                 320

Asn Ile Lys Leu Glu Asn His Thr Gln Cys Tyr Cys Ser Thr Cys Tyr
                325                 330                 335

His His Lys Ile
            340

<210> SEQ ID NO 5
<211> LENGTH: 906
<212> TYPE: DNA
<213> ORGANISM: Artificial Sequence
<220> FEATURE:
<223> OTHER INFORMATION: Nucleotide sequence encoding NTP-BetaCTP-Alpha

<400> SEQUENCE: 5
atggagaccc tgcagggcct gctgctgtgg atgctgctgt ccgtgggagg cgtgtgggct    60
ggcgatatcg gcctgaacat caccggctct ggcctgaata tcacaggatc tggcctgaac   120
attaccggat ccggcctgaa atcaccggc cctggctcca cagatatcag ccggggacca   180
ctgaggcctc tgtgccggcc tatcaacgcc acactggccg ctgagaagga ggcttgccca   240
atctgtatca ccttcaccac atctatctgc gccggctact gtccaagcat ggtgcgcgtg   300
atgccagccg ctctgccagc tatccctcag ccagtgtgca cctatcggga gctgaggttc   360
gcttctatca ggctgccagg atgtccacct ggagtggacc ctatggtgag ctttccagtg   420
gctctgtcct gccactgtgg cccttgccag atcaagacca cagactgtgg cgtgtttagg   480
gatcagccac tggcttgtgc tcctcaggct agctcctcta gcaaggatcc acccagccag   540
cccctgacca gcacatccac cccaacacct ggagctagcc ggaggtcctc tcacccactg   600
cccatcaaga catccttccc agacggcgag tttaccacac aggattgccc cgagtgtaag   660
ctgagggaga caagtacttt ctttaagctg ggcgtgccaa tctatcagtg caagggctgc   720
tgtttctcca gagcctaccc tacaccagct agatctcgca gaccatgctg gtgcccaag   780 aatatcacct ctgagagcac atgctgcgtg gccaaggctt ttatccgggt gaccgtgatg   840
ggcaacatca gctggagaa tcacacccag tgctactgtt ctacatgtta tcaccacaag   900
atctga                                                              906

<210> SEQ ID NO 6
<211> LENGTH: 301
<212> TYPE: PRT
```

<213> ORGANISM: Artificial Sequence
<220> FEATURE:
<223> OTHER INFORMATION: Recombinant protein NTP-BetaCTP-Alpha

<400> SEQUENCE: 6

```
Met Glu Thr Leu Gln Gly Leu Leu Leu Trp Met Leu Leu Ser Val Gly
1               5                   10                  15

Gly Val Trp Ala Gly Asp Ile Gly Leu Asn Ile Thr Gly Ser Gly Leu
            20                  25                  30

Asn Ile Thr Gly Ser Gly Leu Asn Ile Thr Gly Ser Gly Leu Asn Ile
        35                  40                  45

Thr Gly Pro Gly Ser Thr Asp Ile Ser Arg Gly Pro Leu Arg Pro Leu
    50                  55                  60

Cys Arg Pro Ile Asn Ala Thr Leu Ala Ala Glu Lys Glu Ala Cys Pro
65                  70                  75                  80

Ile Cys Ile Thr Phe Thr Thr Ser Ile Cys Ala Gly Tyr Cys Pro Ser
                85                  90                  95

Met Val Arg Val Met Pro Ala Ala Leu Pro Ala Ile Pro Gln Pro Val
            100                 105                 110

Cys Thr Tyr Arg Glu Leu Arg Phe Ala Ser Ile Arg Leu Pro Gly Cys
        115                 120                 125

Pro Pro Gly Val Asp Pro Met Val Ser Phe Pro Val Ala Leu Ser Cys
    130                 135                 140

His Cys Gly Pro Cys Gln Ile Lys Thr Thr Asp Cys Gly Val Phe Arg
145                 150                 155                 160

Asp Gln Pro Leu Ala Cys Ala Pro Gln Ala Ser Ser Ser Lys Asp
                165                 170                 175

Pro Pro Ser Gln Pro Leu Thr Ser Thr Ser Thr Pro Thr Pro Gly Ala
            180                 185                 190

Ser Arg Arg Ser Ser His Pro Leu Pro Ile Lys Thr Ser Phe Pro Asp
        195                 200                 205

Gly Glu Phe Thr Thr Gln Asp Cys Pro Glu Cys Lys Leu Arg Glu Asn
    210                 215                 220

Lys Tyr Phe Phe Lys Leu Gly Val Pro Ile Tyr Gln Cys Lys Gly Cys
225                 230                 235                 240

Cys Phe Ser Arg Ala Tyr Pro Thr Pro Ala Arg Ser Arg Lys Thr Met
                245                 250                 255

Leu Val Pro Lys Asn Ile Thr Ser Glu Ser Thr Cys Cys Val Ala Lys
            260                 265                 270

Ala Phe Ile Arg Val Thr Val Met Gly Asn Ile Lys Leu Glu Asn His
        275                 280                 285

Thr Gln Cys Tyr Cys Ser Thr Cys Tyr His His Lys Ile
    290                 295                 300
```

<210> SEQ ID NO 7
<211> LENGTH: 891
<212> TYPE: DNA
<213> ORGANISM: Artificial Sequence
<220> FEATURE:
<223> OTHER INFORMATION: Nucleotide sequence encoding NTP-Beta-NTP-Alpha

<400> SEQUENCE: 7

```
atggagaccc tgcagggcct gctgctgtgg atgctgctgt ccgtgggagg cgtgtgggct    60
ggcgatatcg gcctgaacat caccggctct ggcctgaata tcacaggatc tggcctgaac    120
attaccggat ccggcctgaa tatcaccggc cctggctcca cagatatctc tcggggacca    180
```

```
ctgaggcctc tgtgcagacc aatcaacgcc accctggccg ctgagaagga ggcttgcccc      240
atctgtatca cattcaccac aagcatctgc gccggctact gtccatccat ggtgagagtg      300
atgccagccg ctctgccagc tatcccacag cccgtgtgca cctatagaga gctgcgcttc      360
gcttctatca gactgccagg atgtccacct ggagtggacc ctatggtgag ctttccagtg      420
gccctgtcct gccactgtgg cccttgccag atcaagacca cagactgtgg cgtgtttcgc      480
gatcagccac tggcttgtgg ctctggcctg aacatcacag gcagtggcct gaatattacc      540
ggctccggcc tgaacattac cggttccggc ctgaatatta ctggaccagg cagcacatcc      600
ttccctgacg gcgagtttac cacacaggat tgccccgagt gtaagctgcg cgagaacaag      660
tacttcttta agctgggcgt gcctatctat cagtgcaagg gctgctgttt ctctcgggct      720
taccctaccc cagctcggag caggaagaca atgctggtgc caagaatat cacctctgag       780 agcacatgct gcgtggccaa ggctttatc cgggtgaccg tgatgggcaa catcaagctg        840
gagaatcaca cccagtgcta ctgttccaca tgttatcacc acaagatctg a                891
```

<210> SEQ ID NO 8
<211> LENGTH: 296
<212> TYPE: PRT
<213> ORGANISM: Artificial Sequence
<220> FEATURE:
<223> OTHER INFORMATION: Recombinant protein NTP-Beta-NTP-Alpha

<400> SEQUENCE: 8

```
Met Glu Thr Leu Gln Gly Leu Leu Trp Met Leu Leu Ser Val Gly
 1               5                  10                  15

Gly Val Trp Ala Gly Asp Ile Gly Leu Asn Ile Thr Gly Ser Gly Leu
                20                  25                  30

Asn Ile Thr Gly Ser Gly Leu Asn Ile Thr Gly Ser Gly Leu Asn Ile
            35                  40                  45

Thr Gly Pro Gly Ser Thr Asp Ile Ser Arg Gly Pro Leu Arg Pro Leu
        50                  55                  60

Cys Arg Pro Ile Asn Ala Thr Leu Ala Ala Glu Lys Glu Ala Cys Pro
65                  70                  75                  80

Ile Cys Ile Thr Phe Thr Thr Ser Ile Cys Ala Gly Tyr Cys Pro Ser
                85                  90                  95

Met Val Arg Val Met Pro Ala Ala Leu Pro Ala Ile Pro Gln Pro Val
            100                 105                 110

Cys Thr Tyr Arg Glu Leu Arg Phe Ala Ser Ile Arg Leu Pro Gly Cys
        115                 120                 125

Pro Pro Gly Val Asp Pro Met Val Ser Phe Pro Val Ala Leu Ser Cys
    130                 135                 140

His Cys Gly Pro Cys Gln Ile Lys Thr Thr Asp Cys Gly Val Phe Arg
145                 150                 155                 160

Asp Gln Pro Leu Ala Cys Gly Ser Gly Leu Asn Ile Thr Gly Ser Gly
                165                 170                 175

Leu Asn Ile Thr Gly Ser Gly Leu Asn Ile Thr Gly Ser Gly Leu Asn
            180                 185                 190

Ile Thr Gly Pro Gly Ser Thr Ser Phe Pro Asp Gly Glu Phe Thr Thr
        195                 200                 205

Gln Asp Cys Pro Glu Cys Lys Leu Arg Glu Asn Lys Tyr Phe Phe Lys
    210                 215                 220

Leu Gly Val Pro Ile Tyr Gln Cys Lys Gly Cys Cys Phe Ser Arg Ala
225                 230                 235                 240
```

Tyr Pro Thr Pro Ala Arg Ser Arg Lys Thr Met Leu Val Pro Lys Asn
            245                 250                 255

Ile Thr Ser Glu Ser Thr Cys Cys Val Ala Lys Ala Phe Ile Arg Val
            260                 265                 270

Thr Val Met Gly Asn Ile Lys Leu Glu Asn His Thr Gln Cys Tyr Cys
            275                 280                 285

Ser Thr Cys Tyr His His Lys Ile
    290                 295

<210> SEQ ID NO 9
<211> LENGTH: 1062
<212> TYPE: DNA
<213> ORGANISM: Artificial Sequence
<220> FEATURE:
<223> OTHER INFORMATION: Nucleotide sequence encoding CTP-Beta-CTP-CTP-Alpha

<400> SEQUENCE: 9

```
atggagaccc tgcagggcct gctgctgtgg atgctgctgt ccgtgggagg cgtgtgggct      60
ggcgtgttcc gggaccagcc tctggcttgc gctccacagg cttccagctc ttccaaggat     120
ccccccttctc agccactgac ctctacatcc accccaacac caggagcttc aggcggagc     180
tctcaccctc tgccaatcaa gacctccagc agaggaccac tgaggcctct gtgcaggccc     240
atcaacgcca ccctggctgc tgagaaggag gcttgcccta tctgtatcac attcaccaca     300
tccatctgcg ctggctactg tcctagcatg gtgcgcgtga tgccagccgc tctgccagct     360
atcccacagc ccgtgtgcac ctataggag ctgcggttcg ctagcatcag gctgcctgga     420
tgtccaccag gagtggaccc aatggtgagc tttcctgtgg ccctgtcttg ccattgtggc     480
ccatgccaga tcaagaccac agactgtggc gtgtttagag atcagccact ggcctgtgct     540
ccacaggctt cttccagctc taaggaccct ccaagccagc cctgaccag cacatctacc     600
cctaccccag gagctagcag acgctccagc catccactgc caatcaagac ctctgccct     660
caggcctctt ccagctctaa agaccccct tctcagcccc tgacctccac aagcacccca     720
acacctggag cttccaggcg gtccagccat ccactgccca tcaagacaag cttccctgac     780
ggcgagttta ccacacagga ttgcccagag tgtaagctgc gggagaacaa gtacttcttt     840
aagctgggcg tgcccatcta tcagtgcaag ggctgctgtt tctccagggc ctaccctacc     900
ccagctagat cccgcaagac aatgctggtg cctaagaata tcacctctga gtccacatgc     960
tgcgtggcca aggcttttat ccgcgtgacc gtgatgggca acatcaagct ggagaatcac    1020
acccagtgct actgttctac atgttatcac cataagatct ga                       1062
```

<210> SEQ ID NO 10
<211> LENGTH: 353
<212> TYPE: PRT
<213> ORGANISM: Artificial Sequence
<220> FEATURE:
<223> OTHER INFORMATION: Recombinant protein CTP-Beta-CTP-CTP-Alpha

<400> SEQUENCE: 10

Met Glu Thr Leu Gln Gly Leu Leu Leu Trp Met Leu Leu Ser Val Gly
1               5                   10                  15

Gly Val Trp Ala Gly Val Phe Arg Asp Gln Pro Leu Ala Cys Ala Pro
            20                  25                  30

Gln Ala Ser Ser Ser Ser Lys Asp Pro Pro Ser Gln Pro Leu Thr Ser
        35                  40                  45

Thr Ser Thr Pro Thr Pro Gly Ala Ser Arg Arg Ser His Pro Leu
    50                  55                  60

Pro Ile Lys Thr Ser Ser Arg Gly Pro Leu Arg Pro Leu Cys Arg Pro
65                  70                  75                  80

Ile Asn Ala Thr Leu Ala Ala Glu Lys Glu Ala Cys Pro Ile Cys Ile
                85                  90                  95

Thr Phe Thr Thr Ser Ile Cys Ala Gly Tyr Cys Pro Ser Met Val Arg
            100                 105                 110

Val Met Pro Ala Ala Leu Pro Ala Ile Pro Gln Pro Val Cys Thr Tyr
            115                 120                 125

Arg Glu Leu Arg Phe Ala Ser Ile Arg Leu Pro Gly Cys Pro Pro Gly
130                 135                 140

Val Asp Pro Met Val Ser Phe Pro Val Ala Leu Ser Cys His Cys Gly
145                 150                 155                 160

Pro Cys Gln Ile Lys Thr Thr Asp Cys Gly Val Phe Arg Asp Gln Pro
                165                 170                 175

Leu Ala Cys Ala Pro Gln Ala Ser Ser Ser Lys Asp Pro Pro Ser
            180                 185                 190

Gln Pro Leu Thr Ser Thr Ser Thr Pro Thr Pro Gly Ala Ser Arg Arg
            195                 200                 205

Ser Ser His Pro Leu Pro Ile Lys Thr Ser Ala Pro Gln Ala Ser Ser
    210                 215                 220

Ser Ser Lys Asp Pro Pro Ser Gln Pro Leu Thr Ser Thr Ser Thr Pro
225                 230                 235                 240

Thr Pro Gly Ala Ser Arg Arg Ser Ser His Pro Leu Pro Ile Lys Thr
                245                 250                 255

Ser Phe Pro Asp Gly Glu Phe Thr Thr Gln Asp Cys Pro Glu Cys Lys
            260                 265                 270

Leu Arg Glu Asn Lys Tyr Phe Phe Lys Leu Gly Val Pro Ile Tyr Gln
            275                 280                 285

Cys Lys Gly Cys Cys Phe Ser Arg Ala Tyr Pro Thr Pro Ala Arg Ser
            290                 295                 300

Arg Lys Thr Met Leu Val Pro Lys Asn Ile Thr Ser Glu Ser Thr Cys
305                 310                 315                 320

Cys Val Ala Lys Ala Phe Ile Arg Val Thr Val Met Gly Asn Ile Lys
                325                 330                 335

Leu Glu Asn His Thr Gln Cys Tyr Cys Ser Thr Cys Tyr His His Lys
            340                 345                 350

Ile

<210> SEQ ID NO 11
<211> LENGTH: 915
<212> TYPE: DNA
<213> ORGANISM: Artificial Sequence
<220> FEATURE:
<223> OTHER INFORMATION: Nucleotide sequence encoding Beta-CTP-CTP-
      Alpha

<400> SEQUENCE: 11
atggagaccc tgcagggcct gctgctgtgg atgctgctgt ctgtgggagg cgtgtgggct      60
tccaggggac cactgcggcc tctgtgcaga cctatcaacg ccaccctggc cgctgagaag    120
gaggcttgcc caatctgtat cacattcacc acaagcatct cgctggcta ctgtccctct    180 atggtgagag tgatgccagc cgctctgcca gctatcccac agcccgtgtg cacctataga    240
gagctgcgct tcgcttctat cagactgcca ggatgtccac ctggagtgga ccctatggtg    300

```
tcctttccag tggccctgag ctgccactgt ggaccatgcc agatcaagac cacagactgt    360
ggcgtgtttc gcgatcagcc actggcttgt gctcctcagg cttccagctc ttccaaggac    420
ccaccctccc agcctctgac ctccacaagc accccaacac ccggcgcttc taggcggagc    480
tctcaccctc tgccaatcaa gacctccgcc ccccaggcct ctagctcttc caaggatcct    540
ccaagccagc tctgacctc tacatccacc cccacacctg gcgctagcag acgcagctct    600
catccactgc ccatcaagac atctttccca gacggcgagt ttaccacaca ggattgcccc    660
gagtgtaagc tgcgcgagaa caagtacttc tttaagctgg gcgtgcctat ctatcagtgc    720
aagggctgct gtttctccag ggcctaccct accccagcta ggagccggaa gacaatgctg    780
gtgccaaaga atatcaccag cgagtctaca tgctgcgtgg ccaaggcttt tatccgggtg    840
accgtgatgg gcaacatcaa gctggagaat catacccagt gctactgttc acatgttat    900 caccataaga tctga                                                     915

<210> SEQ ID NO 12
<211> LENGTH: 304
<212> TYPE: PRT
<213> ORGANISM: Artificial Sequence
<220> FEATURE:
<223> OTHER INFORMATION: Recombinant protein Beta-CTP-CTP-Alpha

<400> SEQUENCE: 12

Met Glu Thr Leu Gln Gly Leu Leu Leu Trp Met Leu Leu Ser Val Gly
1               5                   10                  15

Gly Val Trp Ala Ser Arg Gly Pro Leu Arg Pro Leu Cys Arg Pro Ile
            20                  25                  30

Asn Ala Thr Leu Ala Ala Glu Lys Glu Ala Cys Pro Ile Cys Ile Thr
        35                  40                  45

Phe Thr Thr Ser Ile Cys Ala Gly Tyr Cys Pro Ser Met Val Arg Val
    50                  55                  60

Met Pro Ala Ala Leu Pro Ala Ile Pro Gln Pro Val Cys Thr Tyr Arg
65                  70                  75                  80

Glu Leu Arg Phe Ala Ser Ile Arg Leu Pro Gly Cys Pro Pro Gly Val
                85                  90                  95

Asp Pro Met Val Ser Phe Pro Val Ala Leu Ser Cys His Cys Gly Pro
            100                 105                 110

Cys Gln Ile Lys Thr Thr Asp Cys Gly Val Phe Arg Asp Gln Pro Leu
        115                 120                 125

Ala Cys Ala Pro Gln Ala Ser Ser Ser Lys Asp Pro Pro Ser Gln
    130                 135                 140

Pro Leu Thr Ser Thr Ser Thr Pro Thr Pro Gly Ala Ser Arg Arg Ser
145                 150                 155                 160

Ser His Pro Leu Pro Ile Lys Thr Ser Ala Pro Gln Ala Ser Ser Ser
                165                 170                 175

Ser Lys Asp Pro Pro Ser Gln Pro Leu Thr Ser Thr Ser Thr Pro Thr
            180                 185                 190

Pro Gly Ala Ser Arg Arg Ser Ser His Pro Leu Pro Ile Lys Thr Ser
        195                 200                 205

Phe Pro Asp Gly Glu Phe Thr Thr Gln Asp Cys Pro Glu Cys Lys Leu
    210                 215                 220

Arg Glu Asn Lys Tyr Phe Phe Lys Leu Gly Val Pro Ile Tyr Gln Cys
225                 230                 235                 240

Lys Gly Cys Cys Phe Ser Arg Ala Tyr Pro Thr Pro Ala Arg Ser Arg
```

-continued

```
                  245                 250                 255
Lys Thr Met Leu Val Pro Lys Asn Ile Thr Ser Glu Ser Thr Cys Cys
            260                 265                 270

Val Ala Lys Ala Phe Ile Arg Val Thr Val Met Gly Asn Ile Lys Leu
            275                 280                 285

Glu Asn His Thr Gln Cys Tyr Cys Ser Thr Cys Tyr His His Lys Ile
    290                 295                 300
```

RECOMBINANT CHORIONIC GONADOTROPIN, PROCEDURE FOR PREPARATION, PHARMACEUTICAL COMPOSITIONS AND USES OF THE SAME

RELATED APPLICATIONS

The present application is § 371 filing based on International Application No. PCT/EP2019/073277, filed Aug. 30, 2019, the entirety of which is incorporated herein by reference.

REFERENCE TO APPENDIX [CD ROM/SEQUENCE LISTING]

The instant application contains a Sequence Listing, which has been submitted electronically in ASCII format and is hereby incorporated by reference in its entirety. This ASCII copy, created on Apr. 1, 2022, is named "120971.PF087US_SEQ LISTING_ST25.txt" and is 26,373 bytes in size.

BACKGROUND ART

Equine chorionic gonadotropin (eCG) is a hormone produced by the endometrial cups of the pregnant mare (Christakos and Bahl, 1979). Formerly known as Pregnant Mare Serum Gonadotropin (PMSG), the hormone is commonly used to induce ovulation before artificial insemination in livestock activity. It is a highly glycosylated glycoprotein composed of two α- and β-heterodimeric chains. The Alpha subunit is common to all glycoprotein hormones (LH, FSH, TSH, CG), while the Beta subunits are specific to each hormone and are responsible for the specificity of receptor binding, although in the case of GC it binds to the same receiver as the LH. In equidae (horses, donkeys, zebras), placental CG and pituitary LH are expressed from the same gene and, therefore, have the same protein sequence, which differ only by their carbohydrate side chains, particularly located in the beta subunit, so the consensus also calls them eLH/CG (Sherman et al., 1992).

The eLH and eCG are encoded by the same genes as described above and have an O-glycosylated C-terminal extension and an N-glycosylation in its Beta subunit, in addition to two N-glycosylations in its Alpha subunit (Murphy and Martinuk, 1991), but when expressed and secreted in different tissues they differ strongly in their carbohydrate side chains N and O (Smith et al. 1993, Matsui et al. 1994, Bousfield and Butnev 2001), which gives them different biological powers in vivo due to a longer half-life of the eCG compared to eLH (Klett et al. 2003), as well as different thermal stabilities (Galet et al. 2004).

The production of eCG is currently performed by bleeding pregnant mares that secrete the hormone between 40 and 130 days of gestation (Allen and Moor, 1972). Once purified, formulated and controlled, it is marketed to be used to artificially induce estrus in female goats, cows and pigs, among others. The eCG has two outstanding characteristics for use in the livestock industry, unlike what happens in horses that only has luteinizing activity, in the other species it has the activities of both follicle stimulating hormone (FSH) and luteinizing hormone (LH), and on the other hand, due to its quaternary structure and its multiple glycosylation sites, a half-life in the elevated bloodstream (Stewart et al., 1976; Combarnous et al., 1981).

The current production procedure has all the problems related to the production and purification of an extractive hormone, especially related to the maintenance and health costs of the animals, as well as the difficulties in maximizing the purity of the final formulation. It is therefore very important to be able to develop an alternative method of production.

We know that the differences in the biological activity of the eLH secreted by the hypophysis and the eCG secreted by the trophoblast is fundamentally attributable to the difference in the length and sialylation of its glycans. In addition, it is also clear that the lack of adequate glycosylations in recombinant protein production systems has so far prevented a recombinant eLH/CG with sufficient plasma half-life to show biological activity in vivo.

The document "Expression of a single BETA ALPHA chain protein of equine LH/CG in milk of transgenic rabbits and its biological activity." Galet et al, published in Molecular and Cellular Endocrinology 174 (2000) 31-40, teaches the construction of a beta/alpha chain fusion protein, without the addition of a linker. Said construction is expressed in milk of transgenic rabbits. Although the protein obtained has similar in vitro activity to the native one, it has no activity in vivo and the half-life of the recombinant hormone produced is very low.

On the other hand, in "Biological Activities of Tethered Equine Chorionic Gonadotropin (eCG) and Its Deglycosylated Mutants." MIN Kwan-Sik et al., published in Journal of Reproduction and Development, Vol. 50, No. 3, 2004, they prove a fusion of the Beta and Alpha chains in CHO-K1 cells, with and without mutations that decrease their glycosylation, and do not use any linker to fuse the alpha and beta chains. These researchers only evaluate in vitro activity (cell culture) for both LH and FSH activity and is lower in mutants that are not glycosylated. Although they get active hormones, they are only in vitro.

Attempts to obtain recombinant hormones reported in "Biological activities of recombinant equine luteinizing hormone/chorionic gonadotropin (eLH/CG) expressed in Sf9 and Mimic insect cell line." Legardinier, et al., Journal of Molecular Endocrinology (2005) 34, 47-60, which shows the expression of the Beta and Alpha chains separately in SF9 and Mimic insect cells (SF9 with five added glycosyltransferases) were also not successful. The two eLH/CG produced in the Sf9 and Mimic cells were active in in vitro bioassays of LH and FSH, with potencies similar to those of eCG, but did NOT exhibit significant in vivo bioactivity, nor as a follicle stimulating hormone (FSH) or in the eCG specific assay. Although the recombinant eLH/CG produced in Mimic cells is more glycosylated than those produced in Sf9 cells, they did NOT have differences in the in vivo activity, due to insufficient terminal sialylation of their carbohydrate chains, leading to their rapid elimination of the blood.

Another group reports in "Expression and bioactivity of a single chain recombinant equine luteinizing hormone (reLH)." Jablonka-Shariff et al. Theriogenology 67 (2007) 311-320 the fusion of the Beta and Alpha chains without using any linker. Expression is done in CHO-K1 cells. They describe LH activity in vitro (testosterone production by Leydig cells) and in vivo, also by a peak in testosterone production in horses. However, they do not show the existence of FSH activity. The researchers, knowing that LH produced in the pituitary is less glycosylated than the GC produced in the trophoblast, the recombinant product (reLH) that they get resembles more eLH than eCG and, therefore, argue that CHO cells lack the appropriate glycosyltransferase activity required for eCG synthesis.

Finally, Sogayar et al., in patent application WO 2017/112987 A1, report the transformation of CHO dg44 cells (a CHO K1 line know out for the dhfr gene with a fusion as described in Jablonka-Shariff), select them and amplify and select high production clones of recombinant glycosylated eCG. They evaluate that their CHO cells express all the enzymes involved in glycosylation and that is why their eCG would be active in vitro and in vivo (rats and cows). However, the proposed procedure requires the selection of certain clones that by chance glycosylate with profiles similar to the trophoblast, so that the stability of said clones makes the usefulness of said strategy for scale production relative.

That is why we decided to modify the structure of the eLH/CG in order to increase the chances that it will be glycosylated post-translationally more efficiently in a recombinant expression system without altering its affinity for its receptors, increase its hydrodynamic volume and consequently its biological activity in vivo.

SUMMARY

This invention relates to a recombinant single chain chorionic gonadotropin polypeptide, characterized in that the polypeptide has an amino acid sequence encoding the beta chain and the alpha chain of the equine chorionic gonadotropin linked to one or more sequences that include glycosylation sites.

In one preferred embodiment, the recombinant single chain chorionic gonadotropin polypeptide has an amino acid sequence selected from the group consisting of SEQ ID NO: 2, SEQ ID NO: 4, SEQ ID NO: 6, SEQ ID NO: 8 and SEQ ID NO: 10.

The DNA molecules that encode the recombinant polypeptide are also a relevant embodiment of this application. In particular, the ones that have a sequence selected from the group consisting of SEQ ID NO: 1, SEQ ID NO: 3, SEQ ID NO: 5 and SEQ ID NO: 7.

An expression vector comprising these DNA molecules is also an object of this application.

In one embodiment, these polypeptides are part of a pharmaceutical composition.

These recombinant proteins and compositions are useful for the manufacture of medicaments for the treatment of conditions related to mammal reproduction or ovulation, such as superovulation, ovulation failure, ovarian subfunction, induction of postpartum estrus or hypoorchidia in mammals such as bovines, pigs, sheeps, dogs, rabbits, cervidae, goats and laboratory animals.

Another embodiment refers to a process for producing a recombinant single chain chorionic gonadotropin polypeptide, by transfecting the vector, expressing it in a CHO cell and optionally purifying it immunoaffinity.

DESCRIPTION OF THE DRAWINGS

FIG. 7 shows measurements of FSH biological activity in vitro of stably protein-producing clones.

DETAILED DESCRIPTION

Obtaining Recombinant Variants of the eCG Alpha-Beta Fusion Protein

Herein we describe the production of a single recombinant Alpha/Beta chain of eCG (reCG) with the addition of glycosylation sites to increase its plasma half-life. The construction of a single chain allows the introduction of a sequence of multiple glycosylation sites as a linker and avoids the problem of association/dissociation of subunits.

To do this we modified the gene sequence by adding two sequences with multiple O-glycosylation or N-glycosylation sites. The O-glycosylation sequence is characteristic of the Beta chain and is characterized by being in the Carboxy Terminal Peptide (CTP), the N-glycosylation sequence is designed from the consensus sequence of N-glycosylation in mammals and we call it NTP as opposed to CTP because it is used at the Amino (N) terminal peptide.

Figure 1:
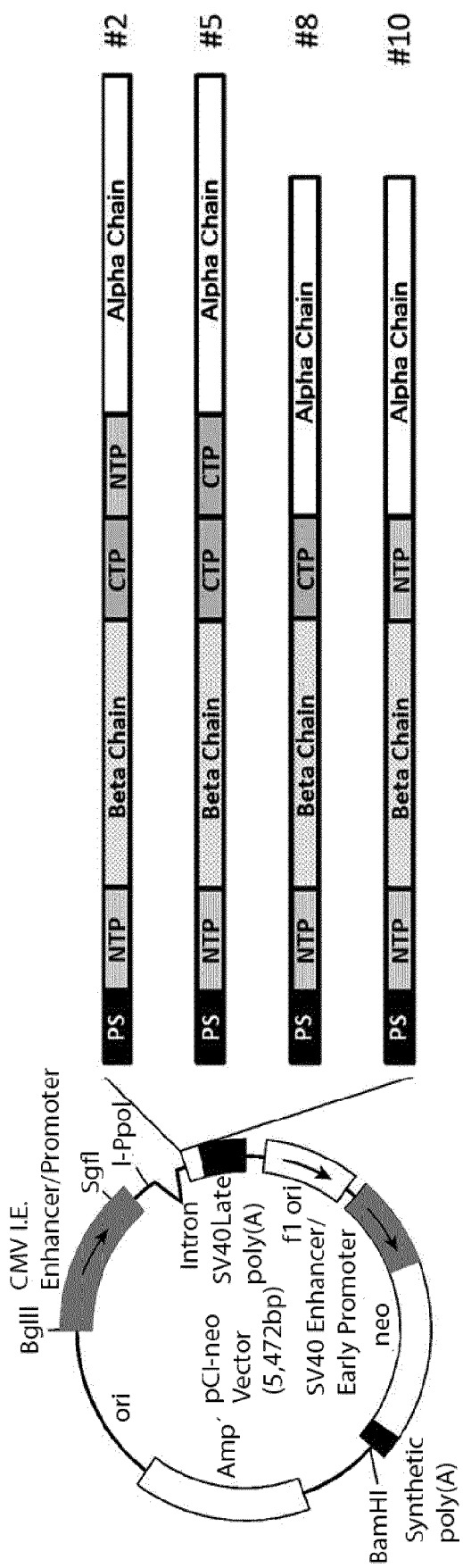
FIG. 1 shows expression vectors that allow to obtain variants of the Beta/Alpha fusion protein linked by different linkers.

In order to evaluate the functionality of different linkers, expression vectors comprising various constructs were prepared, as described in FIG. 1. The nucleotide and amino acid sequences of each of these variants are presented in the attached Sequence Listing:

SEQ ID NO: 1 corresponds to the polynucleotide sequence of the construct encoding NTP-BetaCTP-NTP-Alpha (CONSTRUCT #2) and SEQ ID NO: 2 to its amino acid sequence. SEQ ID NO: 3 corresponds to the polynucleotide sequence of the construct encoding NTP-BetaCTP-CTP-Alpha (CONSTRUCT #5) and SEQ ID NO: 4 to its amino acid sequence. SEQ ID NO: 5 corresponds to the polynucleotide sequence of the construct encoding NTP-BetaCTP-Alpha (CONSTRUCT #8) and SEQ ID NO: 6 to its amino acid sequence. SEQ ID NO: 7 corresponds to the polynucleotide sequence of the construct encoding NTP-Beta-NTP-Alpha (CONSTRUCT #10) and SEQ ID NO: 8 to its amino acid sequence. SEQ ID NO: 9 corresponds to the polynucleotide sequence of the construct encoding CTP-BetaCTP-CTP-Alpha (CONSTRUCT #6) and SEQ ID NO: 10 to its amino acid sequence. SEQ ID NO: 11 corresponds to the polynucleotide sequence of the construct encoding BetaCTP-CTP-Alpha (CONSTRUCT #4) and SEQ ID NO: 12 to its amino acid sequence.

Development of a Method of Determining eCG Through Competitive ELISA

The capture antibody (Ab) is a rabbit anti-eCG polyclonal antibody provided by Syntex. Specific immunoglobulins were obtained by purification with an eCG affinity column covalently bound to CL agarose. The tracer was obtained by biotinylation of the sialic residues with alkoxyamine-PEG12-biotin.

Alkaline Streptavidin phosphatase (Strp-FA) was used to quantify the non-displaced Biot-eCG present in the sample or standard curve.

The test is performed on 96-well ELISA plates, the standard curve is constructed with a Std 1 eCG Syntex standard. The alkaline phosphatase concentration is determined using as a substrate 4-nitrophenyl phosphate in 100 mM Tris pH9.2, 1 mM MgCl2. Reading at 405 nm. The dynamic range of the assay is 20-0.16 ng/well.

In Vitro Gonadotropic (FSH) Biological Activity Determination Test

HEK 293T cells were transfected with a plasmid carrying the bovine FSH hormone receptor transgene and the selection antibiotic neomycin. After selecting for antibiotic resistance and amplifying resistant clones, the expression of the bFSH receptor was checked by binding 125I-FSH in the presence or absence of 1 IU of the standard provided by INAME as a competitor to corroborate the specific binding.

The clone that expressed the FSH receptor, binding the ligand with high affinity and that this binding produced a response synthesizing the second messenger cAMP, was transfected with the luciferase reporter construct under the CRE promoter (pGL4 Promega). Cells that possess this construct in the presence of cAMP produce luciferase proportionally to the amount of the second messenger. The enzyme luciferase transforms luciferin in the presence of ATP+O2 into a metabolite and light. This luminescence, when the whole system is assembled, is proportional to the concentration of the analyte that has follicle-stimulating activity. The dynamic range of the test is 12.5-0.4 mU/tube.

Figure 2:
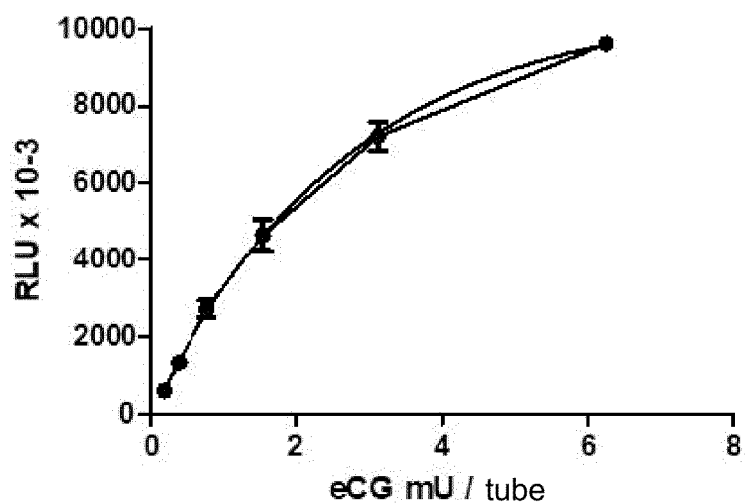
FIG. 2 shows measurements of gonadotropic biological activity (FSH) in vitro, typical dose response curve to eCG.

The typical dose-response curve of in vitro biological activity is shown in FIG. 2.

In Vitro Luteotropic Biological Activity Determination Test

The mouse Leydig cell line constitutively expresses the LH receptor and before a gonadotropic stimulus responds with the cAMP production and progesterone secretion. The current line was recloned by the partial loss of the response to LH/hCG and the clone was selected with the highest response to hCG, it was transfected with the CRE-Luc reporter gene, as were the HEK cells of the FSH activity assay.

The test is carried out on P96 plates coated with collagen by sowing 25,000 cells per well and pre-incubating for 48 hours, then the standard curve of hGC or sample is added continuing incubation for 3 hours. After the stimulation time has elapsed, the culture medium is removed, the reagent being added to determine luciferase activity as in the previous test. The dynamic range of the test is 50-0.8 mIU/well.

Figure 3:
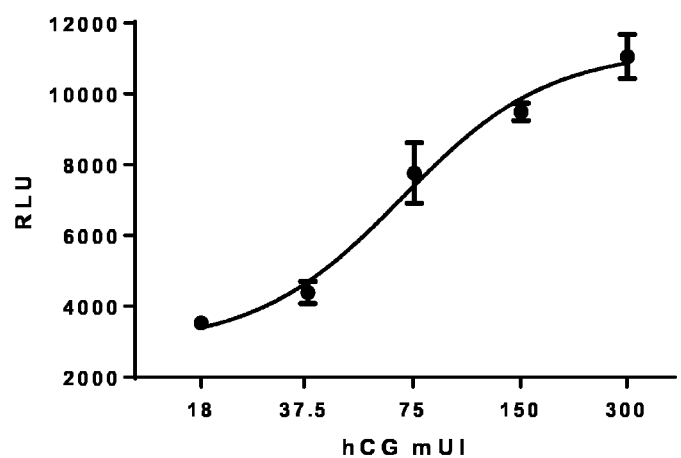
FIG. 3 shows measurements of luteotropic biological activity (LH) in vitro dose response curve to hCG.

The typical dose-response curve to hCG is shown in FIG. 3.

In Vivo Biological Activity Determination Test

The samples were analyzed using the European Pharmacopoeia edition nine (Eh. Ph.9), Equine Chorionic Gonadotropin Monograph for veterinary use, as an analytical standard.

The presence of Equine Chorionic Gonadotropin (eCG), either natural or recombinant, and its consequent biological activity (FSH), should cause in immature female rats injected with the product, an increase in the mass of their ovaries. This increase is determined by comparing the mean weights of the pair of ovaries obtained after treatment, with respect to the weight of the pair of ovaries without treatment (baseline weight). The baseline weight of the pair of ovaries of the strain used in the study (Sprague Dawley (sd)) is below 25 mg.

Methodology: 0.2 mL of the samples were injected subcutaneously to the selected rats.

The injections were repeated 18, 21, 24, 42, and 48 hours after the first injection (keeping the solutions in refrigerator). Animals were sacrificed no less than 40 hours and no more than 72 hours after the last injection. Subsequently, the ovaries were removed separating fat, adhesions and oviduct from each animal and finally both ovaries of each treated rat were weighed.

All animal handling, injection, slaughter, extraction, cleaning and weighing of the ovaries were performed by personnel trained in these methodologies and animal handling.

Female rats of the strain Sprague Dawley (sd) of 21 to 28 days of age (with no more than three days of age apart from each other) and weighing approximately 50-55 g (with a range of ±10 g) were used within the selected group.

Determination of the Functionality of the Constructs

A—Evaluation in HEK293T Cells

For the testing of the gonadotropic activity of the different reCG constructs, the HEK293T cell line was chosen as the synthesis platform for the recombinant proteins. This cell line has the characteristic of having the T antigen that causes the multiplication of plasmids if they have the SV40 gene, this means that with a transient transfection the extraordinary expression of the recombinant proteins cloned in suitable plasmids occurs. It has a disadvantage of a glycosylation pattern that makes recombinant proteins synthesized by this line have a very short half-life once present in complex systems. The activity in systems without clearance in general is not affected and therefore these proteins are used to test the activities in the in vitro systems.

Figure 4:
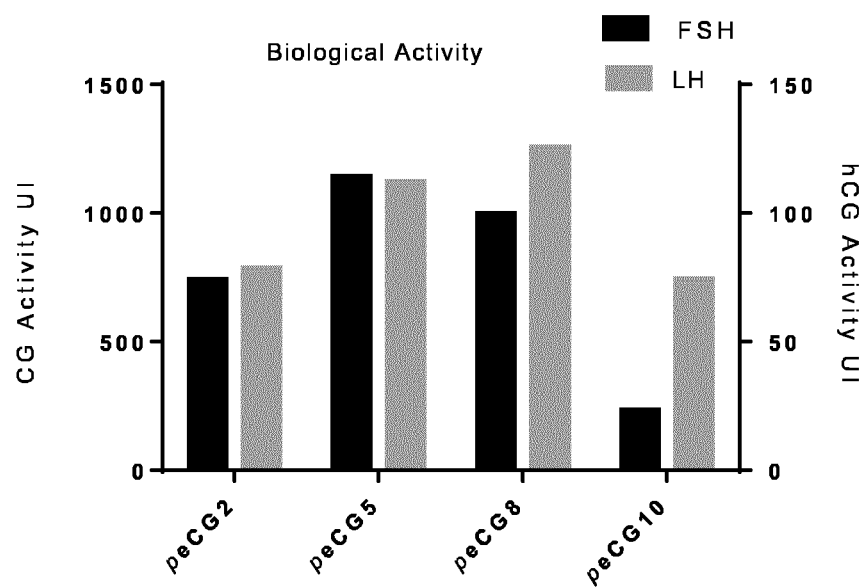
FIG. 4 shows in vitro biological activity measurements for the constructs expressed in HEK293T cells.

In vitro biological activities determined for each of constructs 2, 5, 8 and 10 expressed in HEK293T cells are shown in FIG. 4. The results with HEK cells in vitro, of which FIG. 4 is a typical one, allowed us to conclude that the designed fusion proteins have both eGC activities in vitro.

On the other hand, the in vivo biological activity of these same reCG constructs (recombinant), synthesized in the HEK293T cell line, was studied. The biological activity of the samples was estimated at 500 IU/mL, according to the results obtained from the in vitro tests.

The results obtained, in all cases, show mean ovarian weights below 25 mg, that is, similar to the baseline weight of the strain under study.

Therefore, it is concluded that constructs synthesized in HEK cells, although they have biological activity in vitro, lack biological activity in vivo.

B—Evaluation in CHOK1 Cells

Due to the results obtained in HEK293T cells, the development of reCG was continued, using as platform CHOK1 cells that produce glycoproteins that generally have a plasma half-life greater than HEK and SF9. The constructs of choice were #5 and #8 because they were expressed in greater amounts in the in vitro tests.

Figure 5:
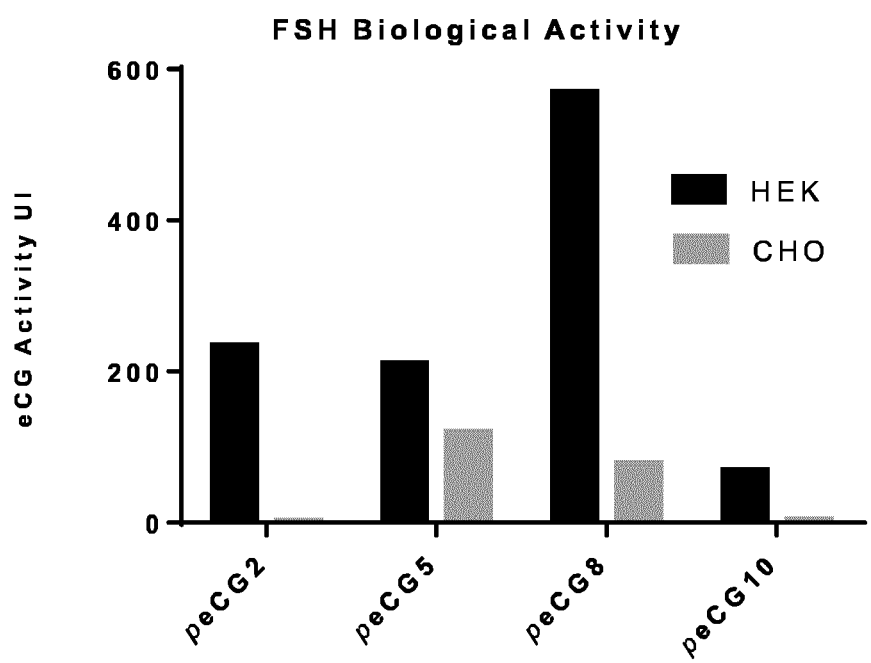
FIG. 5 shows measurements of FSH biological activity in vitro for constructs expressed in HEK293T or CHOK1 cells.

Comparative in vitro FSH biological activities of proteins synthesized by 10×106 HEK or CHO cells are shown in FIG. 5.

Figure 6:
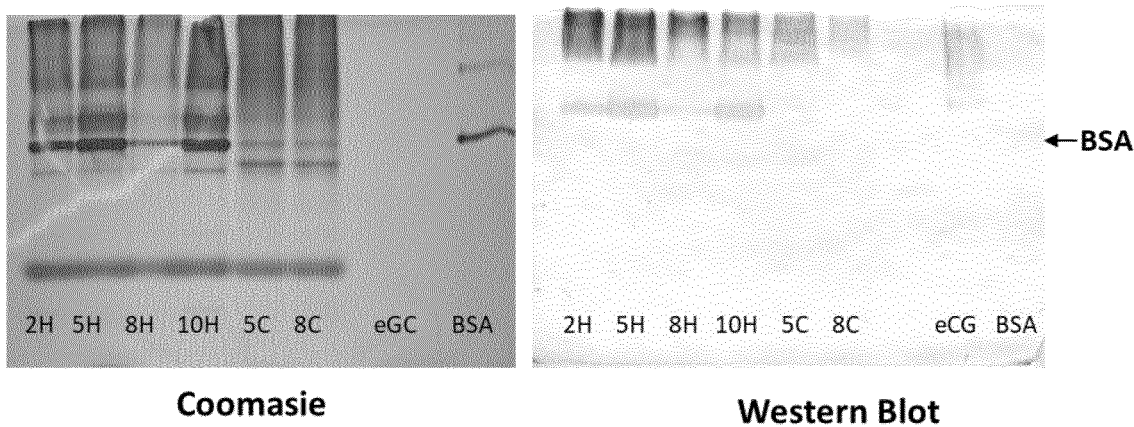
FIG. 6 shows the analysis of the supernatants of the expression products in HEK293T or CHOK1 cells. A 10% native acrylamide gel is shown. Each lane was seeded with 17 ug of total protein. The H series are those synthesized by HEK and C cells in CHO K1. BSA 5 ug and PMSG 0.25 IU. The units corresponding to the 17 ug of mass were: 2H (pCG 2) 4 IU; 5H (pCG 5) 7.2 IU; 8H (pCG.8) 4.5 IU; 10H (pCG 10) 1.4 IU; 5C (pCG5) 0.55 IU; 8C (pCG 8) 0.22 IU.

On the other hand, the proteins present in the supernatants were analyzed in 2 native polyacrylamide gels, using one of them for the detection of total proteins with Coomasie G250 staining and transferring to another Nitrocellulose membrane to analyze it with the antibody generated in rabbits against the eCG Native. The results obtained are shown in FIG. 6.

The apparent size of the recombinant proteins synthesized in HEK cells is similar to the pattern of extractive eGC. This indicates that the lack of observed in vivo activity is not due to the hydrodynamic volume of the polypeptides synthesized in the HEK cells or amount of glycosylation, but to the quality thereof.

Therefore, recombinant proteins produced in CHOK1 cells and with constructs #5 and #8 that are expressed in greater amounts were continued.

The in vivo biological activity test showed an increase in the weight of the ovaries within the minimum stimulation values of the standard curve. The control conditioned medium did not produce values other than the controls.

Given the recognition of the recombinant hormone in the Western blot performed with the antibody generated against the eCG Native, the supernatant of transiently transfected CHO cells was purified with an affinity column with the eCG #5 construct. 13 ug of protein was obtained with an in vitro FSH activity of 61 IU in total. In vivo activity was determined in 3 animals that showed ovarian weights of 203.9 mg, 119.8 mg and 172.9 mg, stimulation values similar to the maximum of the standard curve.

Generation of Stably Protein-Producing Clones

CHO K1 cells were transfected with the eCG #5 and #8 constructs and selected with the G418 antibiotic to obtain cells that stably possess the transgene. Upon reaching confluence the expression of the hormone was determined by ELISA, set up to detect 0.6 ng activities in 50 ul aliquots of supernatant.

The criteria for the selection of the clones was good growth and production greater than 1.5 IU/ml, with 4 clones of constructs #5 and 3 of #8 remaining as candidates. The results are shown in FIG. 7.

Clones 5D, 5G, 5J and 8F were expanded to determine biological activity in vivo and according to the results, clones 5G and 8F were chosen to continue isolation of the recombinant proteins by affinity chromatography of the two constructs for further characterization thereof.

ReCG Purification by Immunoaffinity

Anti eCG immune serum generated in sheep by Syntex was used. The specific IgGs were isolated by affinity with an eCG-Sepharose column obtaining 3 mg of anti-eCG IgG per ml of serum. The aliquots of anti-eCG were dialyzed against coupling buffer (bicarbonate-NaCl) to obtain a total of 90 mg of IgG that was coupled to 9 ml of Sepharose-NHS.

The conditioned media filtered by 0.22 ug were chromatographed at 1 ml/cm2/minute, washed the bed with PBS until returning to baseline and eluted with 3 ml of glycine pH3, collecting the absorbance peak at 280 nm. The glycine eluate pH3 was neutralized, diafiltered against PBS and concentrated.

Figure 8:
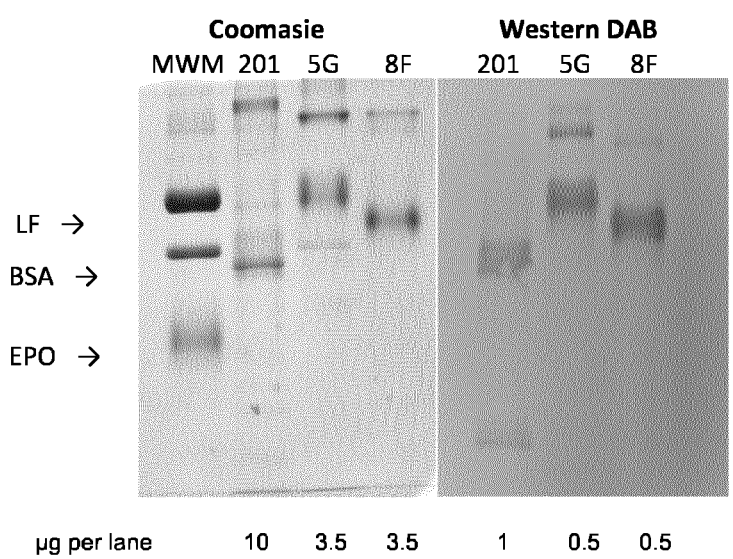
FIG. 8 shows the analysis of purified reCG proteins by immunoaffinity. The eCG pattern seeded was 10 and 1 ug for staining with Coomasie and Western, constructs #5 and #8 were loaded with 3.5 and 0.5 ug for the same conditions.

850 ug of construct #5 and 360 ug of #8 are obtained. They are analyzed by PAGE without reducer, revealing the total protein bands by Coomasie staining and the specific ones by Western Blot using as a first antibody the one generated by Syntex with the native hormone in rabbits. The results are presented in FIG. 8.

It should be noted that in the case of recombinant hormones, the only bands that are revealed with the antibody are the same as those stained with Coomasie. The very high weight bands are possibly dimers of the fusion proteins while the low weight band observed in the native protein is due to the partial dissociation of the heterodimer under the running conditions with SDS but without reducing agents.

Figure 9:
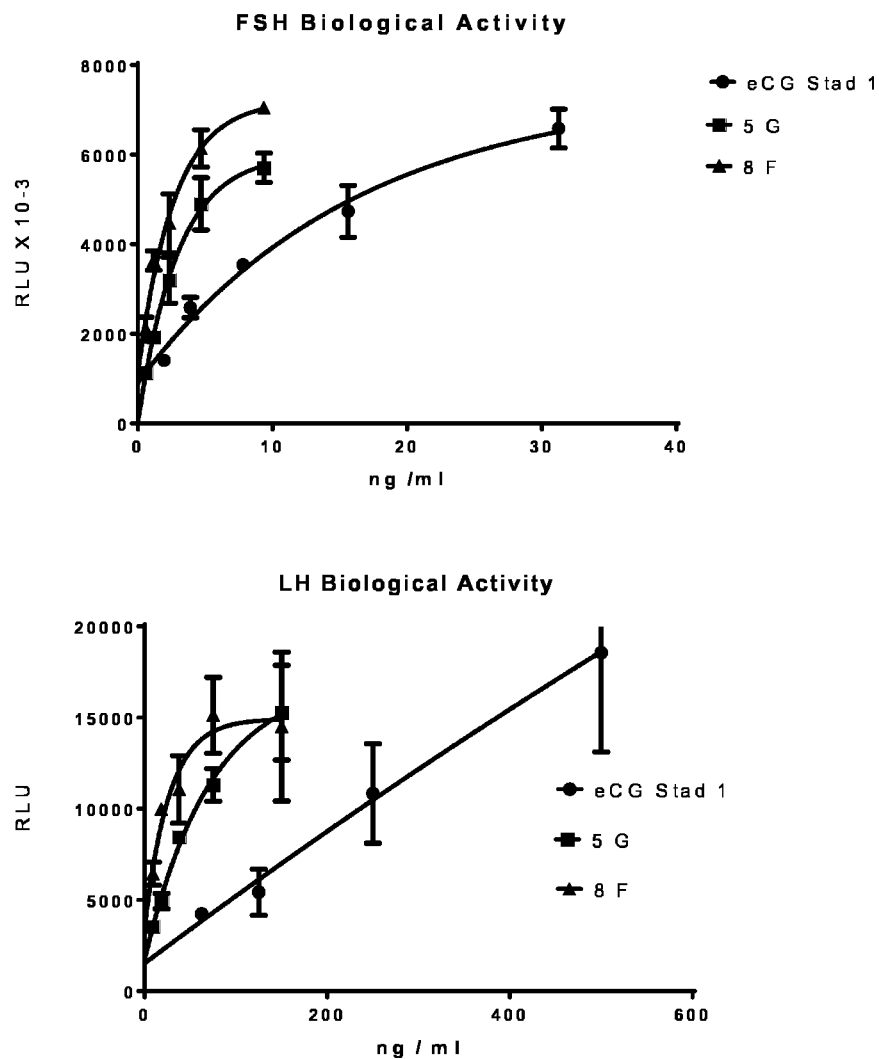
FIG. 9 shows measurements of FSH and LH biological activity in vitro of the stable clones 5G and 8F.

In vitro gonadotropic and luteotropic activities of both proteins and the standard1 eCG Syntex were determined. The results of the dose-response activity of mass and luciferase activity expressed as relative luminescence units (RLU), are presented in FIG. 9. The differences in specific activities between recombinant and native hormones are noticeable, being more noticeable in the case of the luteotropic one, in which the native hormone does not saturate the activity even with the higher doses.

Study of the Biological Activity of the Protein-Producing Clones Stably Generated CHOK1 cells were transfected with constructs #5 and #8 and selected to obtain cells that stably possess the transgene.

The clones of good growth and production were selected, expanding the 5D, 5G, 5J and 8F clones and their biological activity was determined. The results are shown below:

TABLE 3

Biological activity in vivo of stable clones of reCG.

| SAMPLE/ CLONES | Estimated power | Results (mg) Single | Mean Identification | Biological activity |
|---|---|---|---|---|
| 5D | 15 IU/mL | 209.3 | 200.2 positive | present |
|  |  | 183.0 |  |  |
|  |  | 208.4 |  |  |
| 5G | 15 IU/mL | 225.1 | 204.9 positive | present |
|  |  | 199.6 |  |  |
|  |  | 189.9 |  |  |
| 5J | 15 IU/mL | 231.0 | 215.7 positive | present |
|  |  | 232.1 |  |  |
|  |  | 184.0 |  |  |
| 8F | 15 IU/mL | 131.7 | 157.7 positive | present |
|  |  | 163.0 |  |  |
|  |  | 178.3 |  |  |

Due to the results of identification of positive eCG and the high degree of ovarian growth of the treated animals, in comparison with the baseline weights of 25 mg, it is decided to make a first approximation of the evaluation of said samples.

For this, the samples of the different clones are analyzed by the analytical technique based on a standard 3-point eCG curve of different concentration, using the Syntex secondary ecG standard, which was produced in Syntex and valued against the standard: "International Standard NIBSC Code 62/001 (NIBSC)".

Due to the high response in the previous test, the samples are estimated at theoretical powers of 30 IU/mL, the results obtained are seen in the form used to process the raw data obtained:

Determination of Biological Activity in PMSG of a Point

|  | Standard: 2nd SYNTEX Conc. injected inf. from std: 8.1667 Sample | | | |
|---|---|---|---|---|
|  | 5D | 5G | 5J | 8F |
|  | Estimated power | | | |
|  | 30 IU/ml | 30 IU/ml | 30 IU/ml | 30 IU/ml |
| Sample weight (mg) | 5.5 | 5.5 | 5.5 | 5.5 |
| Volume (ml) | 11 | 11 | 11 | 11 |
| Dilution, init. vol. (ml) | 1 | 1 | 1 | 1 |
| Final vol. (ml) | 1 | 1 | 1 | 1 |

Table of ovarian weights (mg) depending on the dose.

| STANDARD | | | | | | |
|---|---|---|---|---|---|---|
| Low | Med. | High | 5D | 5G | 5J | 8F |
| 54.2 | 101.8 | 144.2 | 123.3 | 155.3 | 84.6 | 67.3 |
| 41.2 | 165.1 | 108.4 | 169.3 | 165.3 | 78.7 | 77.4 |
| 122.0 | 172.2 | 95.0 | 131.5 | 204.4 | 142.5 | 71.9 |
| 53.7 | 52.4 | 139.8 | 81.9 | 205.2 | 66.0 | 94.0 |
| 60.2 | 158.4 | 190.2 | 138.5 | 163.0 | 103.7 | 74.4 |
| 62.3 | 134.1 | 132.0 | 139.6 | 167.3 | 107.0 | 34.9 |
| 53.8 | 64.3 | 266.4 | 131.8 | 151.3 | 73.9 | 99.8 |
| 82.6 | 77.2 | 150.4 | 111.6 | 189.5 | 72.9 | 72.4 |

| Batch | Obtained value | Confidence Limit |
|---|---|---|
| 5D | 26 IU/Ml | (24-27) |
| 5G | 33 IU/Ml | (32-34) |
| 5J | 20 IU/Ml | (18-21) |
| 8F | 17 IU/Ml | (16-18) |

It is concluded that the clones analyzed produce a recombinant protein of positive biological activity, with a marked increase in the weight of the ovaries.

All treated animals (8 animals for each sample analyzed) responded to the treatment, without exception.

In addition, comparing with the responses that we know and obtain in animals treated with the natural hormone, the responses evidenced with the recombinant are identical and no strange signals or atypical behaviors are observed in the treated animals.

Due to the data obtained, the powers of the clones are the following:

5D: 26 IU/ml

5G: 33 IU/ml

5J: 20 IO/ml

8F: 17 IU/ml

Study of the Purification Process:

The objective was to evaluate if the purification degraded the molecule or there was a loss thereof as a consequence of the process.

The sample of the 5G construct, which underwent the purification process, was injected into 3 animals. The responses obtained were the following:

203.9 mg-172.9 mg-119.8 mg

Because the growth values are consistent with those obtained with said unpurified clone, it is concluded that the eCG is not lost or degraded during purification.

In the case of construct 8F, subsequent attempts to obtain sufficient mass for in vivo biological activity determinations were negative. Therefore, until the production method has been defined, only construct #5 continues in the progress of the project.

Luteinizing Activity Study (LH):

The biological response of male 21 to 28 days old Sprague Dawley (sd) rats when treated with sample #5 was studied.

Methodology:

A group of 21 to 28 days old Sprague Dawley male rats (sd) (with no more than three days of age between them) and approximately 60-65 grams of weight (with an interval of ±10 grams) of the selected group was prepared.

The sample was injected subcutaneously for 4 consecutive days, in a volume of 0.5 mL every 24 hours.

The rats were sacrificed 24 hours after the last injection, then the seminal vesicles were removed, cleaned, dried with filter paper and weighed.

The tasks of animal manipulation, injection, slaughter, extraction, cleaning and weighing of the seminal vesicles were performed by trained personnel of the animal care facility.

The Sample Solution was prepared by calculating, according to the potency thereof, the mass or volume to be taken and then brought to a concentration of 5,264 IU/mL.

Results: 4 animals were treated, the weights of the seminal vesicles after treatment were as follows:

44.0 mg-58.0 mg-48.0 mg-52.0 mg

Knowing that for the rat strain used the baseline weight of the vesicles (without treatment) is below 12 mg and that within 50 mg the response begins to saturate, we can conclude that the presence of luteinizing activity is verified.

This assay corroborates the dual activity of the recombinant eCG: follicle-stimulating activity and luteinizing activity present.

Determination of the Follicle-Stimulating and Luteinizing Activity of the Final 5G Sample Luteinizing and follicle-stimulating activity were analyzed according to the European Pharmacopoeia edition 9.

Groups of no less than 8 animals were analyzed, using the national INAME standard of hCG and the secondary standard Syntex of eCG.

Results:

| SAMPLE | Estimated potency in vitro | Follicle-stimulating activity in vivo | Luteinizing activity in vivo |
|---|---|---|---|
| 5G | 6200 IU/mg | 6564 IU/mg | 3525 IU/mg |

Based on the above, it is concluded that the recombinant eCG originated from construct #5 has two outstanding activities, both follicle-stimulating (FSH) and luteinizing hormone (LH), similar to the natural hormone.

Determination of the Advantage of Modification by Amino Terminal Peptide Over In Vivo Activity The lack of in vivo biological activity of the fusion proteins using as linker the CTP of the β-chain of the eCG in both the eCG synthesized in SF9 and mimic cells (Legardinier, J Mol Endo (2005) 34), CHO K1 (Min, Endocrine Journal (1996), 43 585-593) or produced in the mammary gland of transgenic rabbits (Galet et al, Mol Cell Endocrinol 174 (2000) 31), indicates the importance of not only the quantity but also the quality of glycosylation. Therefore we tested two alternative constructs to #5, one called #4 which is the fusion of the fused α- and β-chains of the eCG as construct #5 but without modifications in the amino terminal and the other construct #6, similar to #5 in terms of having its amino terminal modified, but in this case with the CTP peptide sequence. This modification evaluates the importance of the amino terminal modification for the same linker sequence.

CHO K1 cells were transfected with the plasmids encoding constructs #4 and #6, and selected for neomycin resistance. Resistant cells were cloned by dilution, choosing those that express the proteins in the greatest amount determined by ELISA (clones 4C and 6A). These were cultured in DMEN-F12 5% SFB medium, the conditioned medium being collected, the proteins were precipitated with ammonium sulfate, suspended in PBS and dialyzed against PBS 36-48 hours with three buffer changes. The concentration of recombinant proteins was determined by ELISA and biological activity in vitro by stimulation of luciferase activity.
eCG construct 4C 13341 IU/mg
eCG construct 5G 4013 IU/mg
eCG construct 6A 4768 IU/mg The greater in vitro biological activity of the protein synthesized by the 4C construct is similar to the results found with the fusion of the beta-alpha chains (Min, Endocrine Journal (1996), 43 585-593). It was also expected that in in vivo systems if this protein showed activity, it is lower than the other recombinant proteins (reCG-5G and reGC-6C).

When these proteins were tested in the in vivo assay, the protein generated with the 5G construct, which has the NTP peptide in the amino terminal, showed an activity of 5477 IU/mg while both the construct with the CTP peptide in the amino terminal and that without modification in it (6A and 4C, respectively) did not produce increases in the ovarian weight of the treated animals.

These data clearly demonstrate that the modification of the amino terminal with the NTP peptide of the fusion protein of the alpha and beta chains of the equine chorionic gonadotropin confers an increase in the half-life and therefore the presence of activity in vivo.

Comparative Field Trials

In order to assess the field behavior of recombinant hormones, it was tested whether intramuscular injection of an estimated dose of 2000 IU of recombinant eCG protein originating from construct #5 (reCG #5) produces the same super-stimulatory and super-ovulatory response that which results from the injection of a 2000 IU dose of eCG Native (Novormon 5000, Syntex).

Progesterone (P4) levels on days 3 and 7 after ovulation are similar in cows treated with a 2000 IU dose of eCG Native or reCG #5.

The trial was carried out at the Santa Julia Zootechnics Station of the Catholic University of Cordoba (UCC) during May, June and July 2019.

14 open Angus/Hereford cows between 3 and 5 years of age were used (the test was carried out in two repetitions of 7 animals per group in each repetition); all the cows presented a corpus luteum at the beginning of the treatment (cyclic). The body condition (BCS) was on average 2.5 (Scale 1-5; Image 1).

The animals are fed ad libitum with alfalfa rolls of good quality and with 15 kg per cow per day of minced silo of corn in two daily feeds administered in feeders and delivered by a tractor with rationing mixer.

Groups of Treatments:

A total of 18 cows was treated on Day −10 of the treatment with a dose of 500 µg of Cloprostenol (Cyclase, Syntex), and heat detection was performed after the application of PGF, 14 cows that showed heat after the PGF were selected to be included in the trial.

All cows (14) were treated on day 0 of treatment with an intravaginal device (DIB, 1 gram of P4, Syntex) plus 2 mg of estradiol benzoate (Gonadiol, Syntex), in order to synchronize the emergence of a new follicular wave on day 4 of treatment approximately (Bo et al, 1994).

On day 4, the cows were divided into two groups to receive 2000 IU of eCG Native (eCG Group, n=7) or a dose of 350 µg of the product produced by Syntex, (reCG Group #5, n=7) which was estimated to be equivalent to 2000 IU of eCG Native. The volume of all the injections was brought to 10 ml and the injection was deep intramuscular.

On day 6.5 of the treatment, a dose of 500 µg of PGF (Cyclase, Syntex) and a second dose were applied on day 7, at which time the devices were removed with P4 (DIB 1 g, Syntex Argentina). A day later (day 8) a dose of 100 µg of GnRH (Gonasyn, Syntex) was applied.

After 20 (day −10 of replication 2) days after the end of repetition 1 (day 17), the cows were treated with the same protocol, but in this case the cows of the eCG Native group were treated with reCG #5 and vice versa. In this way all the cows passed through both treatment groups.

TABLE 4

Replication 1.

| Date | Day of treatment | Activities | |
|---|---|---|---|
| 10-May | Day −10 | PGF | US |
| 20-May | Day 0 | DIB + 2 mg EB | US |
| 24-May | Day 4 | 2000 IU eCG o reCG #5* | US |
| 25-May | Day 5 | | US |
| 26-May | Day 6 | | US |
| 26-May | Day 6.5 | PGF | US |
| 27-May | Day 7 | xDIB + PGF | US |
| 28-May | Day 8 | GnRH | US |
| 29-May | Day 9 | | US |
| 30-May | Day 10 | | US |
| 31-May | Day 11 | | |
| 3-Jun. | Day 14 | | US + Blood |
| 6-Jun. | Day 17 | PGF | US + Blood |

TABLE 5

Replication 2.

| Date | Day of treatment | Activities | |
|---|---|---|---|
| 26-Jun. | Day −10 | PGF | US |
| 6-Jul. | Day 0 | DIB + 2 mg EB | US |
| 10-Jul. | Day 4 | 2000 IU Nov o reCG #5* | US |
| 11-Jul. | Day 5 | | US |
| 12-Jul. | Day 6 | | US |
| 12-Jul. | Day 6.5 | PGF | US |
| 13-Jul. | Day 7 | xDIB + PGF | US |
| 14-Jul. | Day 8 | GnRH | US |
| 15-Jul. | Day 9 | | US |
| 16-Jul. | Day 10 | | US |

TABLE 5-continued

Replication 2.

| Date | Day of treatment | Activities | |
|---|---|---|---|
| 17-Jul. | Day 11 | | |
| 20-Jul. | Day 14 | | US + Blood |
| 23-Jul. | Day 17 | PGF | US + Blood |

*Dose per Cow = 10 ml - im

Ovarian ultrasound scans were performed on the days indicated in Tables 4 and 5 above. The ovarian structures were drawn and recorded on a spreadsheet designed for this purpose.

The animals were examined by means of transrectal ultrasonography (Chison 500; 7.5 MHz, Doppler). All follicles larger than 3 mm in diameter were identified, measured and diagrammed with respect to their location in the ovary, to evaluate the changes in each of them individually. The follow-up technique that was used was the one described in the work of (Knopf et al., 1989) and adapted by Bo (Bo et al., 1994). The data to be evaluated will be: diameter of the dominant follicles and the main subordinates, number of follicles >3 mm present in the ovaries. After injection of eCG or reCG #5, all follicles larger than 8 mm in diameter were identified. After the application of GnRH, ovulation was defined as the disappearance of follicles greater than 8 mm identified in the previous observation. After ovulation, the size and quantity of the corpus luteum (CL) resulting from the ovulations was measured (Adams et al., 1992).

On the other hand, as indicated in Tables 4 and 5, blood samples were taken on days 14 and 17 of the treatments to determine progesterone (P4) levels resulting after ovulations.

Blood samples were obtained by puncturing all the cows in the jugular vein in order to determine plasma progesterone levels. A disposable needle (18 G) was used for each animal and the blood was collected from a sterile 10 ml glass tube with a rubber cap. The samples were always obtained in heparin tubes and immediately after collection they were centrifuged and the plasma was frozen at −20° C., by duplicate (A or B), and duly identified according to the cow tag number, treatment date and hour and either A or B.

The samples were processed by the Immuno chemo luminececia method (ECLIA, COBAS Module e601, Roche).

The mean number of follicles by size (8 to 10 mm, 10 to 12 mm, 12 to 14 mm and >14 mm) and per day of treatment (Day 5, Day 6, Day 7, Day 8, Day 9 and Day 10) were compared by ANOVA.

The mean number of ovulations per day of treatment was compared using the same statistic.

In the same way, the P4 levels were compared on day 14 and 17 of the protocol. In all cases, the treatment group effect, replication and its interaction were considered. Infostat software was used (Di Rienzo et al., 2018).

Results:

A cow from the eCG group in replication 2 withdrew from the trial on day 6 of treatment for respiratory illness. The cow was treated according to the normal procedures of the study center under the supervision of the responsible veterinarian.

No differences were found between the number of follicles (according to size) on any of the days of treatment (P>0.1). There was no replication effect (P>0.07) or replication interaction * group (P>0.4).

TABLE 6

Number of follicles (mean ± SEM) according to the size of the follicles and treatment day in cows treated with eCG (Native; n = 13) or reCG # 5 (n = 14)

| | | ≥8-<10 mm ± SEM | ≥10-<12 mm ± SEM | ≥12-<14 mm ± SEM | ≥14 mm ± SEM |
|---|---|---|---|---|---|
| Day 5 | eCG | 0.46 ± 0.24 | 0.23 ± 0.12 | — | — |
| | reCG #5 | 0.93 ± 0.34 | 0.14 ± 0.10 | — | 0.07 ± 0.07 |
| Day 6 | eCG | 2.62 ± 0.76 | 1.15 ± 0.45 | 0.08 ± 0.08 | — |
| | reCG #5 | 4.07 ± 0.91 | 1.29 ± 0.44 | 0.07 ± 0.07 | 0.14 ± 0.10 |
| Day 7 | eCG | 5.77 ± 1.18 | 5.92 ± 0.8 | 1.46 ± 0.42 | 0.23 ± 0.17 |
| | reCG #5 | 5.21 ± 0.95 | 4.5 ± 0.91 | 1.36 ± 0.56 | 0.36 ± 0.17 |
| Day 8 | eCG | 3.46 ± 1.19 | 4.46 ± 1.08 | 3.46 ± 0.61 | 3.15 ± 0.98 |
| | reCG #5 | 3.86 ± 0.73 | 5.43 ± 1.09 | 3.29 ± 0.51 | 2.43 ± 0.62 |
| Day 9 | eCG | 2.54 ± 0.74 | 2.77 ± 0.75 | 1.23 ± 0.36 | 0.92 ± 0.37 |
| | reCG #5 | 2.79 ± 0.66 | 2.36 ± 0.75 | 1.07 ± 0.30 | 0.5 ± 0.20 |
| Day 10 | eCG | 0.46 ± 0.39 | 0.69 ± 0.54 | — | — |
| | reCG #5 | 0.71 ± 0.34 | — | 0.14 ± 0.10 | — |

Group = P > 0.10
Replication = P > 0.07
Group*Replication = P > 0.4

Figure 10:
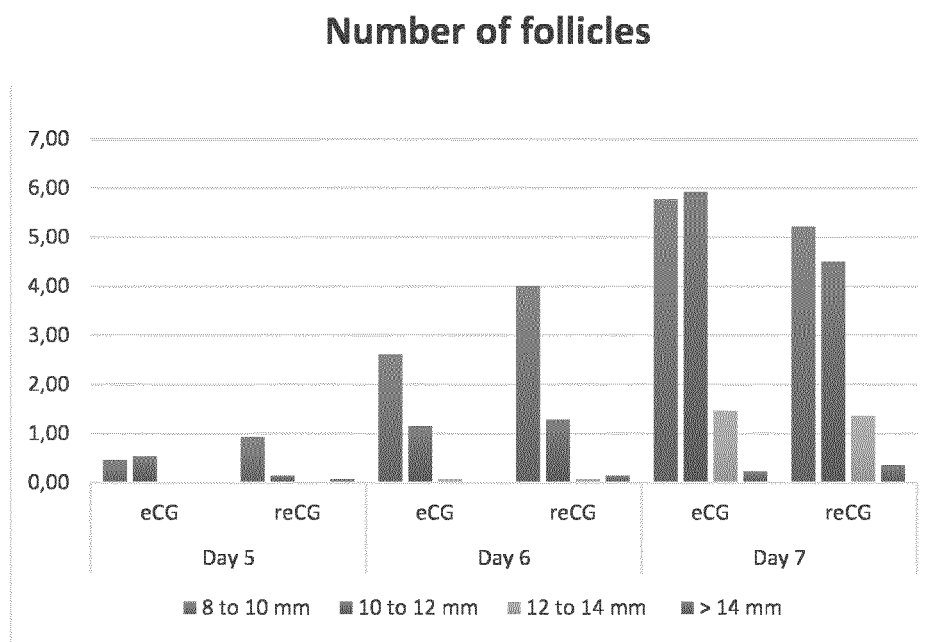
FIG. 10 shows measurements of the number of follicles during treatment with the device with progesterone in field trials in cows. Number of follicles (mean) according to the follicle size and the day of treatment in cows treated with eCG (Native; n=13) or reCG (n=14) during the period prior to removing the device with P4 (P>0.1).

These results are also shown in FIG. 10, in which the information on the number of follicles (divided by size) during treatment with the intravaginal device (days 5 to 7 of the protocol) can be observed. Graphically it can be observed that the amount of follicles present in both groups does not differ.

Figure 11:
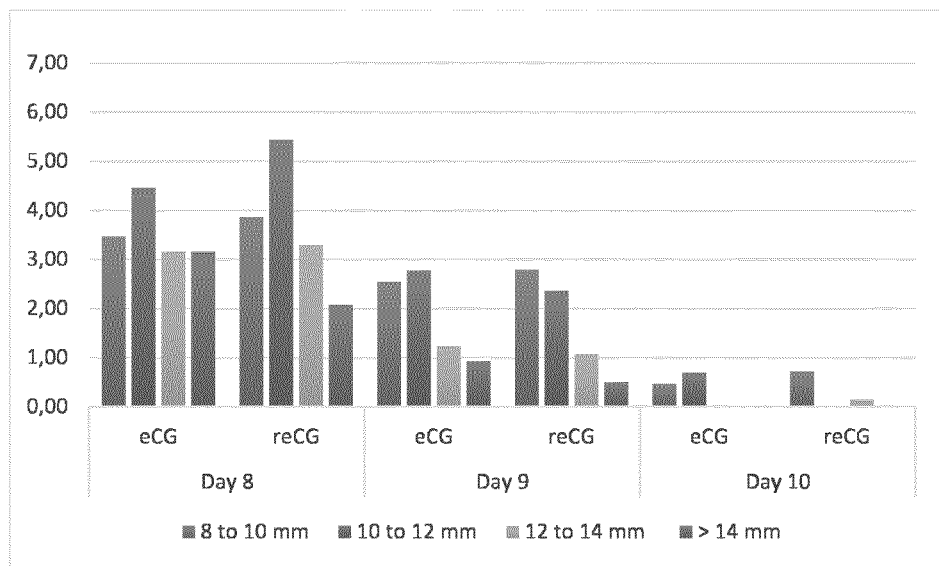
FIG. 11 shows measurements of the number of follicles after removal of the device with progesterone in field trials in cows. Number of follicles (mean) according to the follicle size and the day of treatment in cows treated with eCG (Native; n=13) or reCG (n=14) after removing the device with P4 (P>0.1).

In the same way, in FIG. 11 the number of follicles can be seen after removing the device with progesterone.

The total of diagnosed ovulations (disappearance of follicles >8 mm) occurred between days 9, 10 and 11 (only one cow from the eCG group ovulated on day 11) of the treatment. No differences were found in the number of ovulations between both treatment groups (P=0.83; Table 3). There was also no replication effect (P=0.06) or replication * group interaction (P=0.85).

No differences (P>0.7) were found in the average levels of P4 between both treatment groups on day 14 and 17 of the treatment. Nor was a replication effect found (P>0.9). The following Table shows the results.

TABLE 7

P4 levels in cows treated with 2000 IU of eCG or its equivalent in doses treated with eCG -Like on days 14 and 17 of treatment.

|  | P4 Day 14 Means ± SEM | P4 Day 17 Means ± SEM |
| --- | --- | --- |
| eCG (n = 13) | 45.92 ± 8.67 | 76.45 ± 16.29 |
| eCG - Like (n = 14) | 49.66 ± 8.40 | 77.73 ± 18.54 |

P > 0.7

Figure 12:
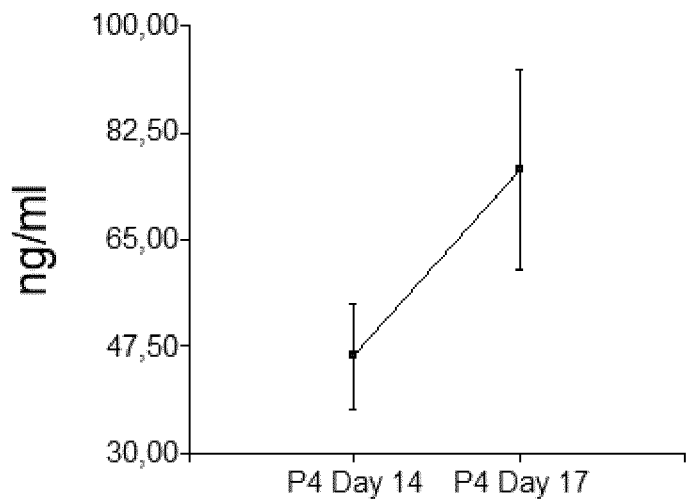
FIG. 12 shows measurements of the number of follicles after removal of the device with P4 levels in both treatment groups.
Figure 12:
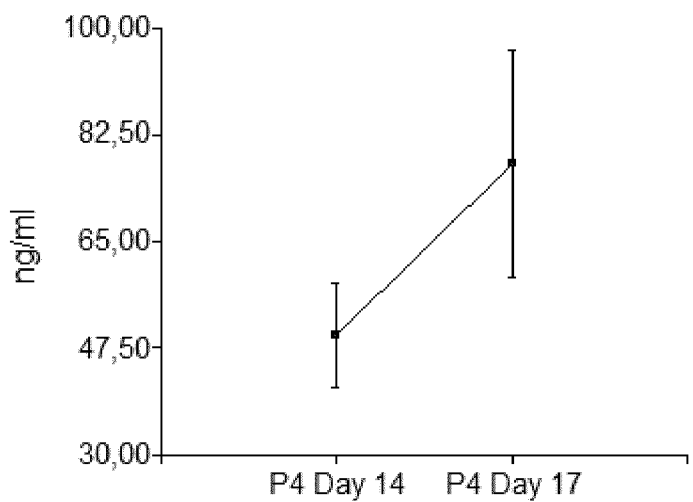

FIG. 12 shows the levels of P4 in both groups and days of sampling.

Based on the results obtained, we can conclude that reCG #5 injected to the test animals results in a gonadotrophic activity similar to that produced by the eCG Native (Novormon). This is because the super-stimulatory response found in both groups of cows was similar before and after the removal of the device with progesterone, as well as the number of ovulation found after the device was removed.

On the other hand, we can infer that the half-life of both products is similar, since the rate of follicular growth was similar in both groups; however, specific trial to determine the half-life should be performed in the future.

The ovulatory rates found in this study, using 2000 IU of eCG, were similar to those reported by other authors using the same dose in bio typically similar cattle (Alfuraiji et al., 1993; Goulding et al., 1996).

No differences were found in P4 levels on days 14 and 17 of treatment, which indicates that the functionality and quantity of luteal bodies present in each treatment group are equivalent to each other.

Finally, and based on the similar response obtained, we believe that the reCG #5 used in this study could be used in lower doses (400 IU) to increase the pregnancy rates obtained in the FTAI programs in anoestrus beef cows in and dairy cows. That is, it could have the same effect as the Native eCG when used for that purpose.

The invention claimed is:

1. A recombinant single chain chorionic gonadotropin polypeptide comprising the amino acid sequence of the beta chain and the alpha chain of equine chorionic gonadotropin linked to one or more sequences that include glycosylation sites,
   wherein said one or more sequences that include glycosylation sites comprise an N-glycosylation sequence (NTP) linked to the N-terminal region of the beta chain, and
   wherein the polypeptide comprises the amino acid sequence selected from the group consisting of SEQ ID NO: 2, SEQ ID NO: 4, SEQ ID NO: 6, and SEQ ID NO: 8.

2. A DNA molecule encoding the recombinant polypeptide of claim 1, and comprising the nucleotide sequence selected from the group consisting of SEQ ID NO: 1, SEQ ID NO: 3, SEQ ID NO: 5, and SEQ ID NO: 7.

3. An expression vector comprising the DNA molecule of claim 2.

4. A pharmaceutical composition comprising the recombinant single chain chorionic gonadotropin polypeptide of claim 1 and a pharmaceutically acceptable vehicle.

5. A process for producing a recombinant single chain chorionic gonadotropin polypeptide, comprising transfecting the expression vector of claim 3 into a mammalian cell.

6. The process of claim 5, wherein the mammalian cell is a CHO cell.

7. The process of claim 6, further comprising purifying the recombinant single chain chorionic gonadotropin by immunoaffinity.

8. A method of treatment of conditions related to reproduction or ovulation of a mammal, comprising administering a therapeutically effective amount of the recombinant chorionic gonadotropin polypeptide of claim 1 or a pharmaceutical composition comprising the therapeutically effective amount of the recombinant chorionic gonadotropin polypeptide to a mammal in need thereof.

9. The method of claim 8, wherein the condition related to reproduction or ovulation of a mammal is selected from the group consisting of:
   superovulation, ovulation failure, ovarian subfunction, induction of postpartum estrus, and hypoorchidia.

10. The method of claim 8, wherein the mammal is selected from the group consisting of: a cow, a pig, a sheep, a dog, a rabbit, a deer, a goat, and a laboratory animal.

* * * * *